United States Patent
Bhide et al.

[11] Patent Number: 6,150,158
[45] Date of Patent: Nov. 21, 2000

[54] AGRICULTURAL PRODUCT MICROSCREEN METHOD AND APPARATUS

[75] Inventors: Arvind Krishna Bhide, Newark, Del.; Carol L. Bush, Rising Sun, Md.; Theodore William Frentzel, Jr., Newark, Del.; Mary Kolean Koeppe, Landenberg, Pa.; Louis G. Rosanio, Jr., Wilmington, Del.

[73] Assignee: E. I. du Pont de Nemours and Company, Wilmington, Del.

[21] Appl. No.: 09/173,287

[22] Filed: Oct. 15, 1998

Related U.S. Application Data

[60] Division of application No. 08/882,000, Jun. 4, 1997, which is a continuation-in-part of application No. PCT/US96/18915, Nov. 26, 1996.
[60] Provisional application No. 60/007,851, Dec. 1, 1995.

[51] Int. Cl.[7] .................................................. C12M 1/32
[52] U.S. Cl. .................................. 435/286.3; 435/288.4; 435/309.1; 435/4; 435/32; 47/14; 47/58.1; 221/211; 221/252
[58] Field of Search ................ 435/286.3, 4, 286.6, 435/32, 309.1, 309.4, 288.4; 47/14, 16, 58.1, 901; 221/211, 252; 73/863.31, 863.32, 864.11, 864.15

[56] References Cited

U.S. PATENT DOCUMENTS

| | | |
|---|---|---|
| 979,175 | 12/1910 | Lapham . |
| 1,057,877 | 4/1913 | Peeples . |
| 2,546,838 | 3/1951 | Tasche . |
| 3,738,530 | 6/1973 | Fine et al. . |
| 3,750,832 | 8/1973 | Ovarnstrom . |
| 3,986,638 | 10/1976 | Dehart . |
| 4,106,414 | 8/1978 | Vastag . |
| 4,230,983 | 10/1980 | Steere et al. . |
| 4,401,236 | 8/1983 | Germaine . |
| 4,573,609 | 3/1986 | Tesch, Jr. . |
| 4,897,345 | 1/1990 | Harris et al. ................................. 435/7 |
| 5,255,618 | 10/1993 | Berry . |
| 5,414,955 | 5/1995 | Morin . |
| 5,562,232 | 10/1996 | Pearson . |

FOREIGN PATENT DOCUMENTS

| | | | |
|---|---|---|---|
| 0 258 565 A2 | 3/1988 | European Pat. Off. | ......... G01N 1/00 |
| 2 661 068-A1 | 4/1990 | France | .............................. A01G 0/02 |
| WO 93/25067 | 12/1993 | WIPO | .............................. A01H 1/04 |

OTHER PUBLICATIONS

Derwent Publications, Ltd., GB; AN 95–008995 [02] (1995).
JP 06 292 461 A, Japan Tobacco Inc., Oct. 21, 1994.
Derwent Publications Ltd., London, GB; AN 84–080089 [13] (1984).
SU 1 020 067A (UKR Plant Protect), May 30, 1983.
Derwent Publications Ltd., London; GB; AN 87–005786 [01] (1987).
SU 1 230 485A (Corn Res. Inst.), Jan. 5, 1986.
D.L. Dornbos, Jr. And G.F. Spencer, Natural Products Phtotoxicity, Journal of Chemical Ecology, vol. 16, No. 2, 1990, pp. 339–351.

*Primary Examiner*—William H. Beisner

[57] ABSTRACT

Methods and apparati for screening compounds for agricultural activity has now been developed which employ e.g., intact plants grown in microtiter plates on very small amounts of plant growth media containing a test compound. In comparison to the standard greenhouse screen, the microscreen requires vastly less space, labor, and test compound. However, unlike in vitro screens, responses of intact plants are assayed. Using the microscreen, high-throughput screening of test compounds can be accomplished using whole plant responses as the assay.

4 Claims, 12 Drawing Sheets

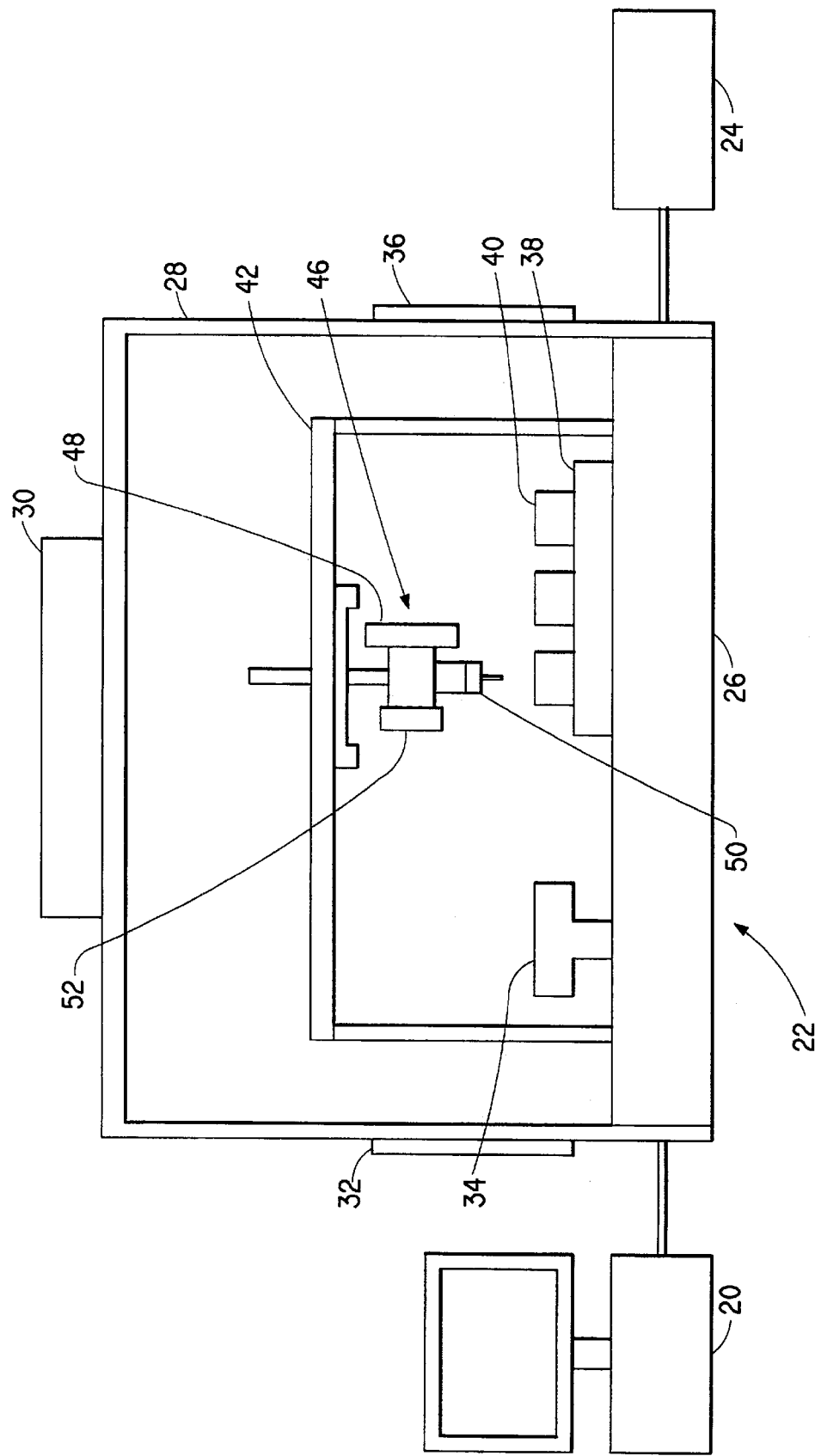

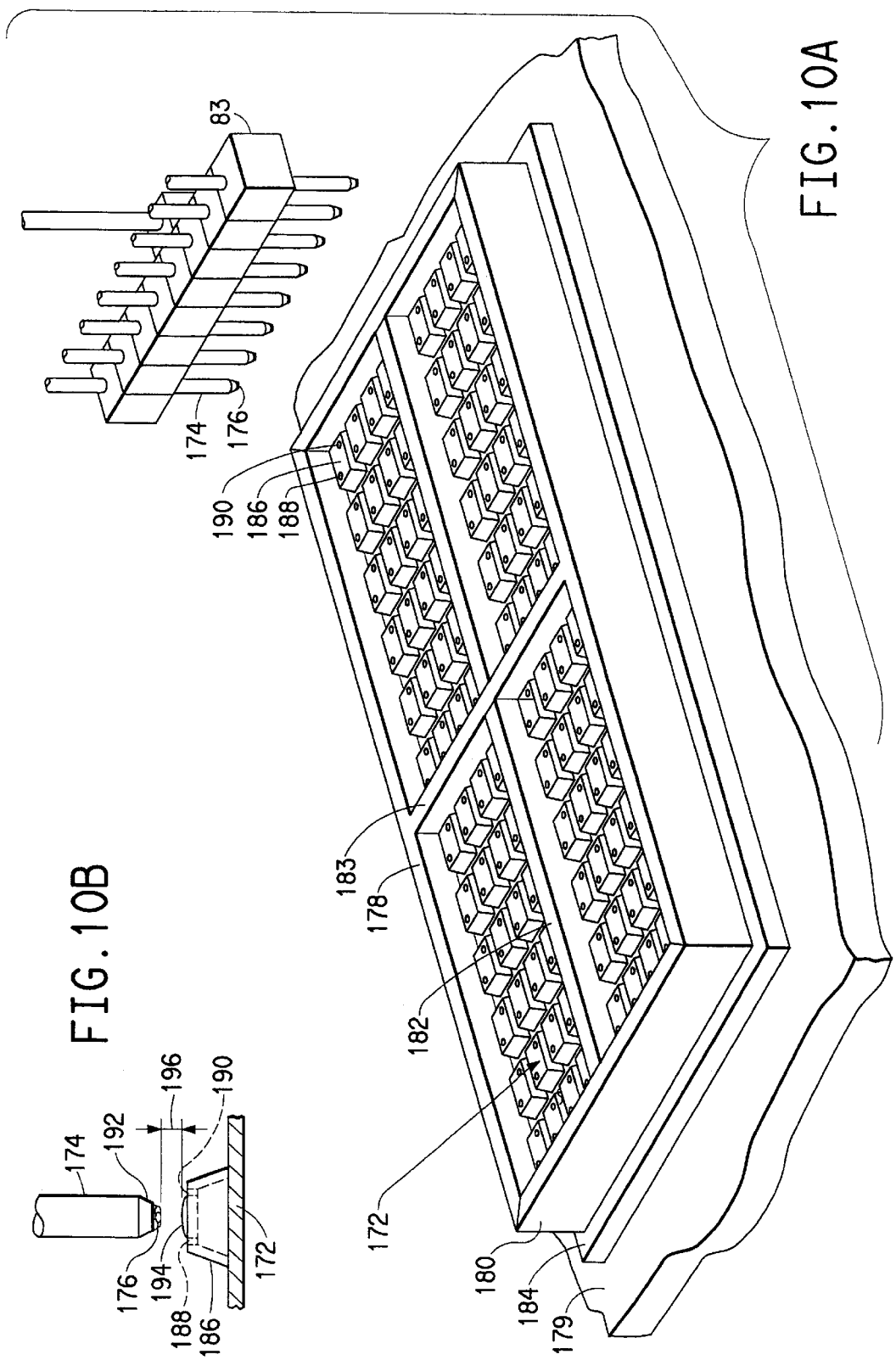

AGRICULTURAL PRODUCT MICROSCREEN METHOD AND APPARATUS

CROSS-REFERENCE TO RELATED APPLICATIONS

This application is a divisional of application Ser. No. 08/882,000, filed Jun. 4, 1997 which is a continuation-in-part of pending Application No. PCT/US96/18915, filed Nov. 26, 1996, which claims benefit of U.S. Provisional Application No. 60/007,851 filed Dec. 1, 1995, now abandoned.

BACKGROUND OF THE INVENTION

Agricultural product candidates are normally identified either by screening test compounds for biological activity on intact plants grown in soil ("greenhouse" assays) or by screening test compounds for inhibition of specific target enzymes or other proteins in vitro ("in vitro" assays). In greenhouse assays, test compounds are either sprayed onto soil containing ungerminated seeds (pre-emergent application) or onto the plants themselves (post-emergent application). Greenhouse assays have a high success rate in predicting the herbicidal activity of a compound when applied in the field. Additionally, a greenhouse assay simultaneously tests for compounds which affect essentially all potential modes of herbicidal action. In other words, greenhouse assays possess a high information content. However, greenhouse testing is time- and space-consuming, requiring 2 weeks and 2 ft$^2$ of greenhouse space for each compound tested. Large amounts of labor are also required to prepare, care for, spray and score these tests. Moreover, 10 to 60 mg of a test compound is required to assess its potential herbicidal activity at normal use rates. The requirement for this amount of test compound places significant limitations on the synthesis or acquisition of compounds to be tested.

In vitro assays, by contrast, typically assay the affect of a test compound on only a specific target enzyme or protein. These targets are usually extracted proteins, and their responses to the test compounds are assayed in vitro. Alternatively, these targets are expressed in surrogate microorganisms and their responses are assayed by their effects on the growth or metabolism of the microorganisms. In either case, these assays have great advantages over greenhouse assays, including much lower space, labor, time and compound requirements. However, the value of these assays for predicting herbicidal or other biological activity under natural conditions is limited by complex and poorly understood processes unique to intact plants which are absent in vitro or in surrogate organisms. Processes such as uptake, translocation, and metabolism of test compounds cannot at present be accurately predicted and must be determined empirically by evaluating responses on intact plants. Moreover, in vitro screens are only capable of screening test compounds against a single or very small number of targets, thus requiring separate assays for each new target.

A method for screening compounds for herbicidal or other biological activity which combines the high information content and good predictive qualities of greenhouse screening with the reduced size, cost and compound requirements of in vitro screens, wherein high-throughput screening of test compounds can be accomplished using whole plant responses as the assay, is desirable.

Dornbos and spencer have examined the germination and early seedling growth of three species of weeds (*Medicago sativa, Lolium multiflorum,* and *Abutilon theophrasti*) in 24-well tissue culture plates (Dornbos, D. L. Jr. and Spencer, G. F. *J. Chem. Ecol.* (1990), 16, 339–351). The wells in these plates were cylinders, about 1.6 cm in diameter and 1.7 cm in height, with a total volume of about 3.4 cm$^3$. Each well contained 1 mL of 0.5% agar in water. Various amounts of test compounds were added to the surface of the agar in 1 mL of solvent (99% hexane, 1% chloroform) and the solvent was then allowed to evaporate. Seeds were placed on the agar and after 3 days, seed germination and seedling length were measured. This assay is terminated at 3 days after inoculation of the seed onto the agar, a point at which the seedlings are still largely dependent on seed reserves for growth. Thus, it is likely that the short term growth will not allow the detection of injury of certain classes of herbicides which affect photosynthetic or other processes which are not required for early seedling growth.

SUMMARY OF THE INVENTION

This invention pertains to a method and apparatus for evaluating at least one compound for its biological activity on plants, the method comprising (a) placing a plant growth medium and at least one seed into contact with each other and into a container having a cross-sectional area measured in the horizontal direction of not greater than 1 cm$^2$, the at least one seed being a seed which will germinate into a plant of the genus selected from the group consisting of Ageratum, Alopecurus, Alternifolius, Arabidopsis, Arabis, Artemisia, Asrostis, Browallia, Capsella, Coleus, Cortaderia, Cynodon, Cyperus, Digitalis, Digitaria, Eragrostis, Festuca, Inula, Ipomopsis, Laevis, Lemna, Lolium, Nicotiana, Oxalis, Panicum, Petunia, Pilifera, Platycodon, Poa, Recta, Sagina, Santolina, Thymophylla, and Thymus, (b) maintaining the container with the medium and at least one seed under conditions such that in the absence of the at least one compound the at least one seed would germinate and the resulting plant would grow, (c) contacting the at least one compound to be evaluated with the at least one seed before germination thereof or with the plant resulting from the germination of the at least one seed, and (d) evaluating the resulting germination or plant growth. Seeds which will germinate into a plant of the genus selected from the group consisting of Ageratum, Arabidopsis, Arabis, Artemisia, Asrostis, Browallia, Capsella, Coleus, Cortaderia, Cynodon, Cyperus, digitalis, Digitaria, Eragrostis, Inula, Ipomopsis, Laevis, Lemna, Nicotiana, Oxalis, Panicum, petunia, Platycodon, Recta, Sagina, Santolina, Thymophylla, and Thymus are preferred in the method of the present invention wherein there is used a standard microtiter plate having 96 or fewer wells. More preferred with such standard microtiter plates is a method wherein the at least one seed is a seed which will germinate into a plant of the genus selected from the group consisting of Arabidopsis, Asrostis, Browallia, Coleus, Digitalis, Digitaria, Eragrostis, Inula, Nicotiana, Oxalis, Panicum and Petunia. Most preferred for use in the method is a seed which will germinate into a plant selected from the group consisting of *Arabidopsis thaliana, Browallia speciosa, Coleus blumei, Digitaria sanguinalis, Nicotiana tabacum,* and *Petunia hybrida.*

The method of the present invention further comprises the method described above wherein the container has a cross-sectional area measured in the horizontal direction substantially smaller than 1 cm$^2$, and in some cases not greater than 1 mm$^2$.

The method of the present invention further comprises the mechanized placing of one and only one seed at a time into each of a plurality of containers as described above, the seed being selected from the group described above, so that each seed will be in contact with a plant growth medium and a compound to be evaluated, each container being maintained under conditions such that in the absence of the compound the seed would germinate into a single plant and the resulting plant would grow in the container. The method further comprises the automated mechanized placing of one and only one seed at a time in each of the containers as described above. The method of the present invention further comprises providing such automated mechanical seeding by providing a supply of seeds in at least one fluidized seed bed, providing a plurality of vertical hollow tubes, each of such tubes having at its lower end an opening the largest dimensions of which is smaller than the smallest dimension of the seed, each of such tubes having means for controlling air pressure within the hollow portion of the tube to be less than, equal to or greater than the air pressure outside of the tube, the air pressure within each tube being individually controllable, positioning the plurality of tubes relative to the at least one fluidized seed beds such that the lower end of the plurality of tubes is partially immersed in the at least one fluidized seed bed, controlling the air pressure within each tube to create a vacuum within each tube sufficient to capture and hold a seed at the opening at the lower end of each tube, positioning the plurality of tubes relative to the containers such that the lower end of each tube is within a container, positioned approximately in the center of the horizontal cross section of each container, below the level of the top of the container and above the level of any contents in the container, controlling the air pressure within each tube to release the vacuum and create pressure within each tube higher than the pressure outside each tube sufficient to release and expel the seed into the container.

The method further comprises having in each container before the seed is expelled therein a substance which when contacted by the seed will inhibit or prevent further movement of the seed within the container and inhibit or prevent the seed from being expelled from the container due to air currents resulting from any excess air pressure within the tube.

The method of the present invention further comprises detecting whether each container has had placed therein one and only one seed, and correcting the seeding of any container found not to contain one and only one seed. The method further comprises such detecting being done automatically by optical scanning techniques.

The present invention further comprises apparatus for carrying out the above-described method, which apparatus is described in greater detail below.

The above described method for placing one and only one seed at a time into each of a plurality of containers and for detecting whether each container has had placed therein one and only one seed is especially well-suited for standard microtiter plates having 96 or fewer wells or containers. For plates having much smaller containers such as the 9600- or 2400-well plates which are described in greater detail below, mechanical placing of one seed per container is not practical, and ensuring that there is one and only one seed per container is not necessary.

BRIEF DESCRIPTION OF THE FIGURES

FIG. 4 is a schematic elevation view of the overall automated seeding system.

FIGS. 10A and 10B are a perspective view and section view, respectively, of a microtiter lid and egg pickup tube for use in egg placement.

DETAILED DESCRIPTION OF THE INVENTION

Figure 1A:
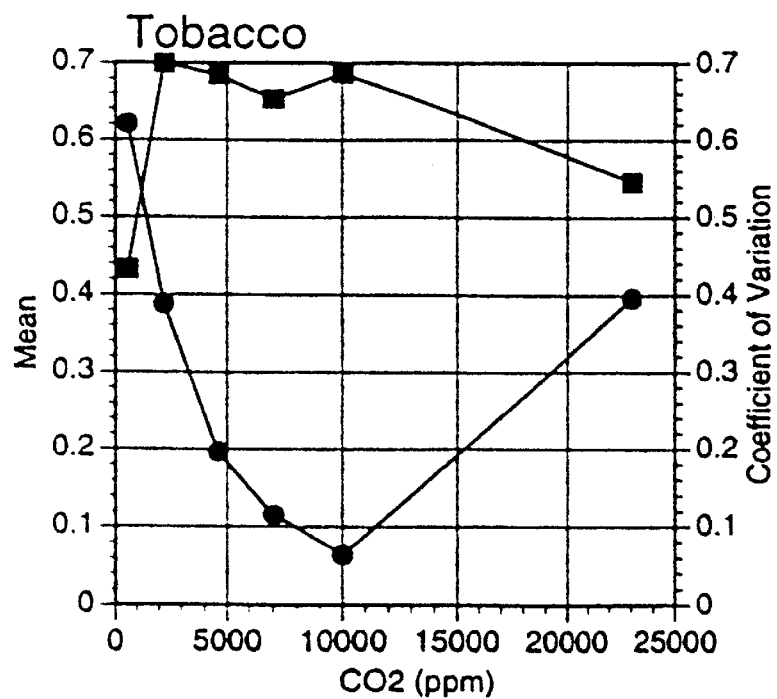
FIGS. 1A–G. Effects of $CO_2$ concentration on growth of seven different species in microtiter plates. Plant species are indicated in each panel. Plates were maintained in plexiglass chambers at the indicated $CO_2$ concentration for 12 days except for Digitaria which was maintained for 7 days. After this incubation period, the chlorophyll content of the plants was determined. The mean (-■-) and coefficient of variation (-●-) of the chlorophyll content per seedling are plotted. Between 32 and 48 individual seedlings were used for each data point. These experiments demonstrate that elevated levels of $CO_2$ have a positive impact on seed germination (mean) and uniformity of plant growth (coefficient of variation) for most of the tested species.
Figure 1B:
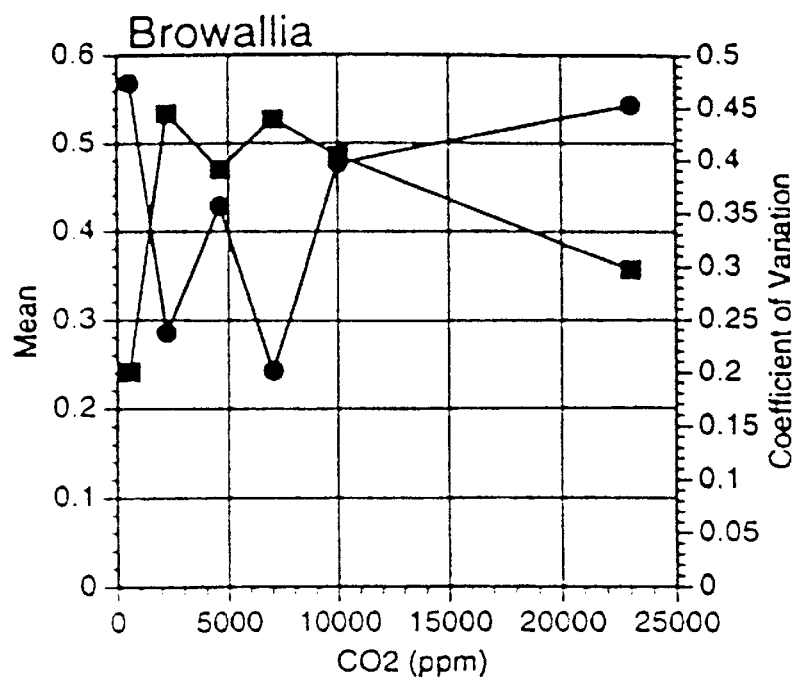
Figure 1C:
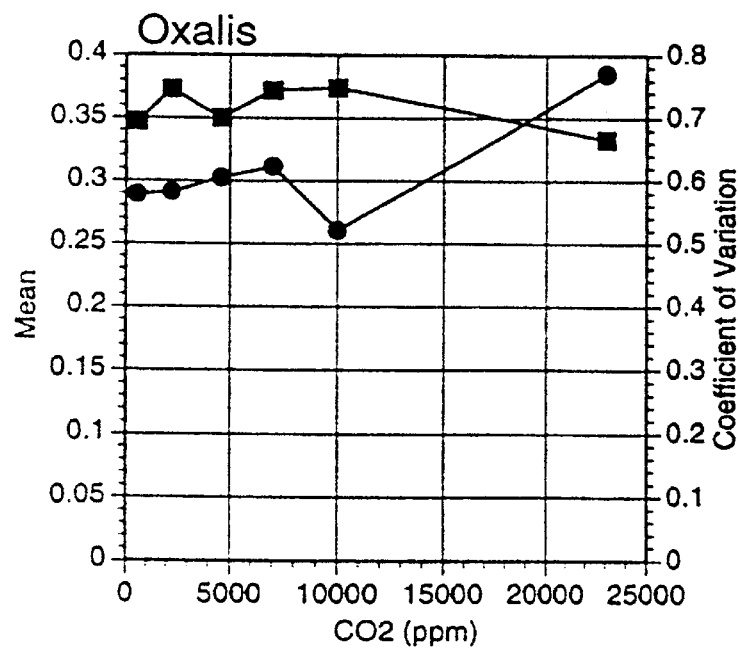
Figure 1D:
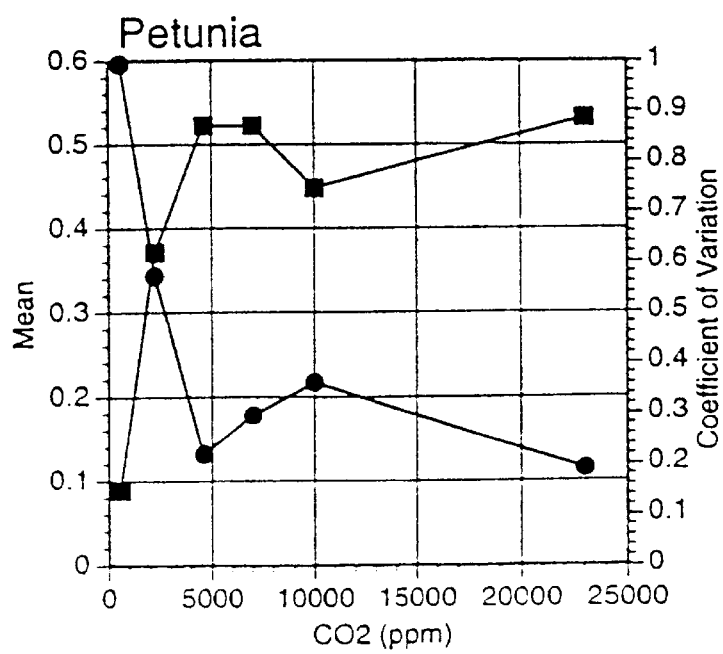
Figure 1E:
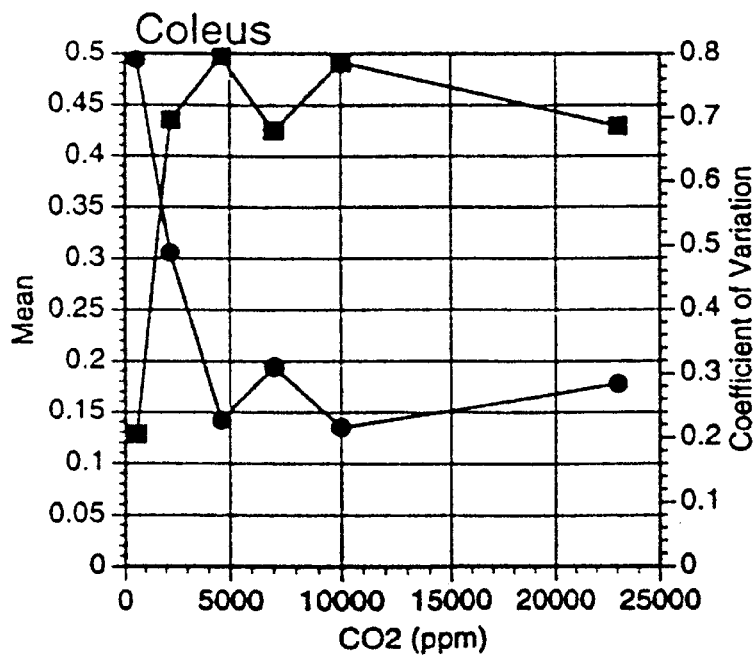
Figure 1F:
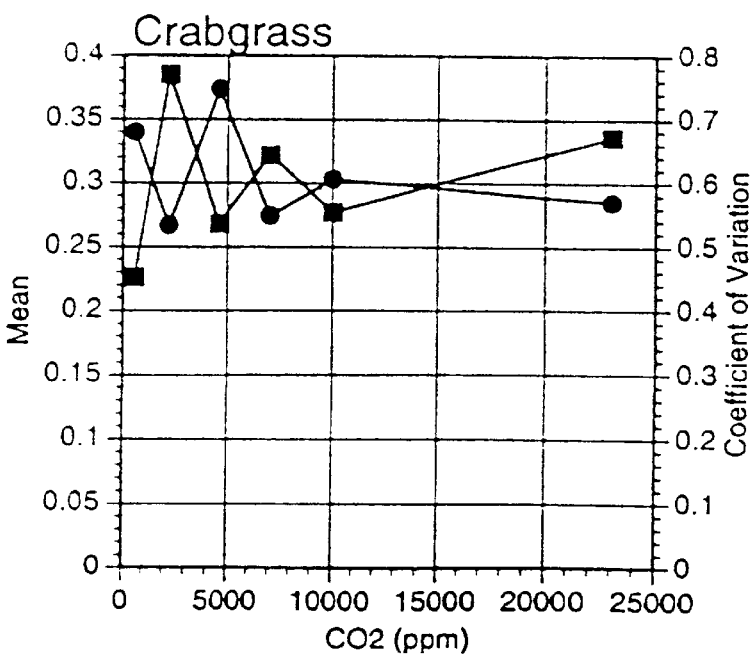
Figure 1G:
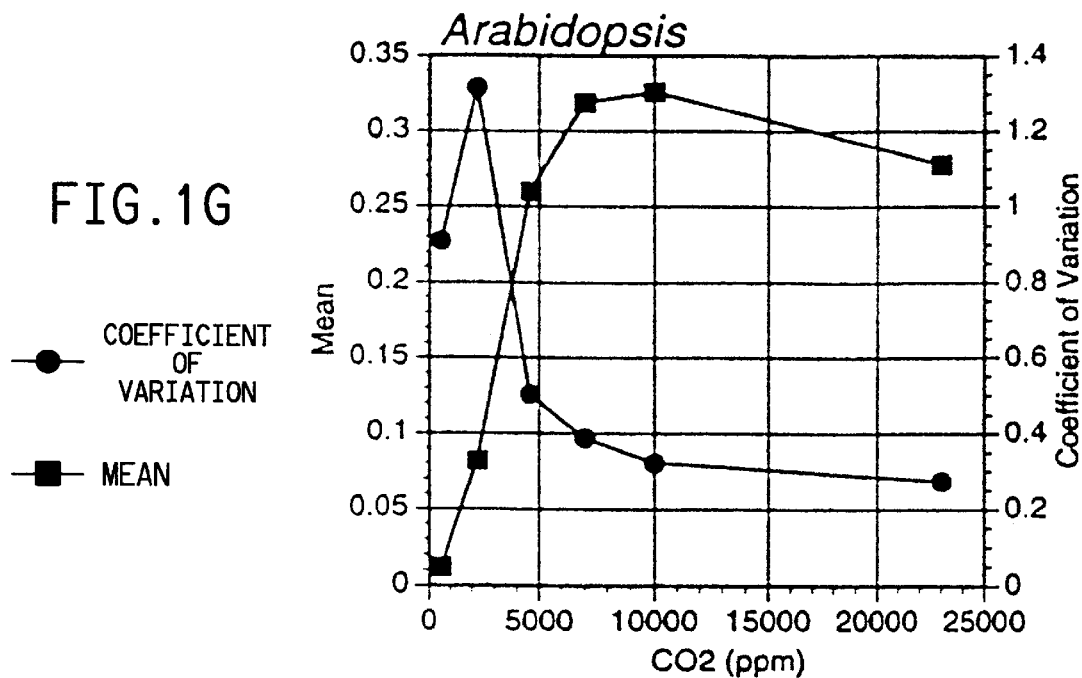

A method for screening compounds (including both synthetic chemical compounds and compounds occurring in nature) for herbicidal activity (termed the herbicide microscreen) has now been developed which combines the high information content and good predictive qualities of greenhouse screening with the reduced size, cost and compound requirements of in vitro screens. This screening method employs intact plants grown in small containers on very small amounts of growth media containing the test compound. In comparison to the standard greenhouse screen, the microscreen requires vastly less space, labor, and test compound. However, unlike in vitro screens, responses of intact plants are assayed. Using the microscreen, high-throughput screening of test compounds can be accomplished using whole plant responses as the assay. This method for detection of compounds and molecules that display herbicidal activity is capable of screening large numbers of candidates in a format that minimizes space, materials, waste stream and labor costs.

The expressions "growth medium" or "growth media" refer to any of a variety of simple or complex mixtures of nutrients in which growth of plant material occurs. In addition, water itself, without specific or deliberate supplementation, can serve as a growth medium in the present invention.

In a preferred embodiment, the container is one of a plurality of containers of substantially the same dimension as each other arranged in a rectangular matrix on a single supporting plate, and the method comprises placing into substantially all of the plurality of containers a growth medium, at least one seed and either at least one compound to be evaluated or a control material. Alternatively, the compound(s) to be tested can be applied post-emergent to plants resulting from the at least one seed. One preferred embodiment of the method exploits a physical format of testing vessels that is in common use in research laboratories and clinical settings. In the most preferred embodiment, this format, commonly referred to as a microtiter plate, generally employs a test unit comprised of a series of wells, known as microwells, wherein the footprint, or the two dimensional space that the unit occupies, is approximately 9 cm by 13 cm. This format is especially convenient in that many instruments have been developed (and are commercially available) that automate plate movement, well filling, aspirating and washing, and data collection from individual microwells. The opening of each microwell of the microtiter plates contemplated by this invention can be square or, preferably, circular, generally with a cross-sectional area of less than 1 cm$^2$, prefereably less than 0.5 cm$^2$. Although a "standard" microtiter plate is comprised of cylindrical microwells arranged in an 8×12 matrix that are approximately 1 cm deep and can accommodate a liquid volume of 300–400 uL, this invention also pertains to other microtiter plates wherein the microwells are deeper ("deep well" microtiter plates) and can therefore accommodate a larger fluid volume, or alternatively wherein there are a greater number of wells per plate (for example, Nunc 384 Well Plate; Cat. No. 242757; Nunc, Inc., Naperville, Ill.). These other microtiter plates maintain the described 9×13 cm footprint, thus facilitating automated handling of microtiter plates in support of the high-throughput nature of the screening method. Deeper wells accommodating a larger fluid volume may be employed in order to afford growth of certain plant species; greater numbers of wells per plate will increase the number of compounds that can be screened per assay plate and reduce the quantities of materials (compounds, growth media) consumed per assay.

Species Selection

Unless otherwise specified, the experiments described herein were conducted under the following conditions. One hundred microliters of molten 0.4% agarose in ½×MS salt media without sugar and vitamins (Murashige, T. and Skoog, F. *Physiol. Plant.* (1962) 15, 485; hereinafter "½×MS") were pipetted into each well of 96 well microtiter plates, allowed to cool and harden, and one seed per well was placed on the top of the agarose using a forceps. The microtiter plates were sealed with gas permeable tape to prevent the growth media from drying out and the plates were placed in an incubator at 25° C./21° C. day/night, 16 h photoperiod (45–80 μmol/m2/s photosynthetically active radiation (PAR)) and 60–90% relative humidity. Plates were kept in plexiglass boxes and were visually rated 14 days after planting (DAP). $CO_2$ concentration was maintained at an artificially high level (approximately 1%) by daily addition of a 1.5 g piece of dry ice to the plexiglass boxes housing the microtiter plates.

A total of 192 species were tested for growth in 96-well microtiter plates. Species were selected for testing based primarily on the small size of their seeds. Seeds were purchased from Germania (Chicago, Ill.) or were propagated at Stine Research Center (DuPont Co, Newark, Del.). Plates were prepared as described above and 24–32 seeds were planted per species. Germination rate and growth habits of each species were observed visually 7 and 14 DAP. All species evaluated were compared using, primarily, ratings (described below) and general growth characteristics. Those species exhibiting appropriate size, shape and uniformity were advanced for additional testing. Germination rate was a factor when species within a single genus were compared. The rating scale used was as follows:

| | |
|---|---|
| Excellent | Ideal plant for microtiter plate growth, strong in all categories (size, shape, uniformity). |
| Good | Nearly ideal, but lacking in one or two categories, weaknesses can probably be overcome. |
| Poor | Will grow, but has glaring weaknesses which may be difficult to overcome. |
| Unacceptable | Will not work in microtiter plates. |

Of the 192 species tested, a total of 68 species were advanced for further testing in ambient and high $CO_2$ (1%) environments. Plants held in a high $CO_2$ environment were grown in sealed plexiglass boxes and 1.5 g dry ice was added daily to achieve the 1% $CO_2$ level. From this test, 35 species (listed in Table 1) were selected which were rated good to excellent as previously described. These 35 species were tested against 18 commercial herbicides representing 10 different modes of action. Table 2 lists the herbicides and modes of action.

TABLE 1

Plant species selected for testing biological response to commercial herbicides.

| Genus | Species | Common Name |
|---|---|---|
| Ageratum | sp. | Ageratum (blue danube) |
| Arabidopsis | thaliana | Arabidosis |
| Arabis | blepharophylla caucasica | Arabis (compinkie) |
| Artemisia | dracunculus | Tarragon |
| Asrostis | stolonifera | Bentgrass |
| Browallia | speciosa | Browallia (marine bells) |
| Browallia | speciosa | Browallia (jingle bell) |
| Capsella | bursa-pastoris | Shepherdspurse |
| Coleus | blumei | Coleus (wizard golden) |
| Coleus | blumei | Coleus (rainbow-strain) |
| Coleus | blumei | Coleus (pink dragon) |
| Cortaderia | selloana-pink | Pampus Grass |
| Cynodon | dactylon | Bermudagrass |
| Cyperus | difformis | Cyperus |
| Digitalis | purpurea | Digitalis (white) |
| Digitalis | purpurea | Digitalis (excelsior) |
| Digitaria | sanguinalis | Large crabgrass |
| Eragrostis | curbula | Weeping lovegrass |
| Inula | ensifolia | Ensifolia |
| Ipomopsis | elegans | Capitata Gilla |
| Laevis | jasione-perennis | Perennis Jasione |
| Lemna | minor | Lemna |
| Nicotiana | tabacum | Tobacco |
| Oxalis | stricta | Yellow woodsorrel |
| Panicum | dichotomiflorum | Fall panicum |
| Panicum | coloratum | Kleingrass |
| Petunia | hybrida | Petunia (star joy) |
| Petunia | hybrida | Petunia (carpet mixture) |
| Petunia | hybrida | Petunia (velvet frost) |
| Platycodon | grandiflorum | Platycodon |
| Recta | warrensii | Potentilla |

TABLE 1-continued

Plant species selected for testing biological response to commercial herbicides.

| Genus | Species | Common Name |
|---|---|---|
| *Sagina* | *subulata* | Pilifera spergula |
| *Santolina* | *chamaecyparissus-tomentasa* | Chamaecyparissus |
| *Thymophylla* | *puntuiloba-dyssodia* | Dahlborg daisy |
| *Thymus* | *vulgaris* | Thyme |

TABLE 2

Commercial herbicides used for testing biological response of 35 species.

| Herbicide | Mode of action |
|---|---|
| cyanazine | photosystem inhibitor |
| metribuzine | photosystem inhibitor |
| betanal | photosystem inhibitor |
| diquat | photosystem inhibitor |
| pyrizone | photosystem inhibitor |
| norfluorazon | carotenoid biosynthesis |
| fluoridone | carotenoid biosynthesis |
| acifluorifin | porphyrin biosynthesis inhibitor |
| trifluralin | mitotic inhibitor |
| 2,4-D | auxin |
| quizolofop ethyl | lipid biosynthesis |
| dichlobenil | cellulose biosynthesis |
| glyphosate | amino acid biosynthesis |
| nicosulfuron | amino acid biosynthesis |
| alachlor | protein synthesis |
| butachlor | protein synthesis |
| propanil | protein synthesis |
| bromoxynil | respiratory inhibitor |

A 10,000 ppm solution of each herbicide was prepared in dimethylsulfoxide (DMSO). Thirty microliters of each solution were dissolved in 9.97 mL ½×MS media to yield a 30 ppm solution. Serial dilutions of the 30 ppm solution were made to prepare 0.3 and 0.003 ppm solutions. Thirty-three microliters of the 30, 0.3 and 0.003 ppm solutions were each pipetted into wells of 96-well microtiter plates. Sixty-six microliters of 0.6% agarose in ½×MS media were added to each well yielding a final concentration of 10, 0.1 and 0.001 ppm in 0.4% agarose. Three plates were prepared at each concentration. Controls contained 33 uL of untreated ½×MS media plus 66 uL of 0.6% agarose (3 plates). One seed of each species was planted in each of 8 wells (12 species per plate). Plants were rated visually for herbicidal injury using a 0–4 rating system (see Table 4) 14 DAP. Species were rated based on one or more of the following criteria:

| | |
|---|---|
| Biological response | Species had low sensitivity to majority of herbicides or activity overlapped directly with other species. |
| Germination rate | Species had <50% germination rate. |
| Growth habit | Species were too large or small and/or did not grow uniformly. |

Based on results of the above test, 11 species were selected for additional testing against the 18 herbicides described in Table 2 at 30, 10 and 1 ppm using similar procedures as described above. The eleven species tested were *Arabidopsis thaliana, Asrostis stolonifera, Browallia speciosa, Coleus blumei, Digitalis purpurea, Digitaria sanguinalis, Eragrostis curbula, Inula ensifolia, Nicotiana tabacum, Panicum coloratum* and *Petunia hybrida*. Plants were visually rated for injury 14 DAP as described in Table 4.

These eleven plant species demonstrated good sensitivity for some herbicidal modes of action at concentrations as low as 0.1 ppm, had good germination rates (>50%) and had a suitable size, shape and uniformity for growth in a microtiter plate well. These tests also served to fine tune the concentration of herbicide necessary for detection of activity. These tests showed that 1 and 10 ppm concentrations were necessary for detecting biological activity across various plant species and herbicidal modes of action.

Media Selection

The eleven species selected were grown in five different media to determine which medium would be best suited for each species. The five media tested were: ½×MS medium (supra), DMG Medium (Datko et al. *Plant Physiol.* (1980) 65, 906–912) Arabidopsis medium without sucrose (Haughn, G. W. and Somerville, C. R. *Mol. Gen. Genet.* (1986) 204, 430–434), ½×Hoagland's nutrient solution (Hoagland, D. R. and Arnon, D. I., (1950) California Agricultural Experiment Station, Circular #347, 32 p) and monocot medium (Armstrong, C. L. and Green, C. E. *Planta* (1985) 164, 207–214).

Table 3 shows the media that worked best for each species. Good growth of all species occurred in any of the tested media. Since ½×MS medium was the best medium for most species, it was selected as the universal medium for this assay, although media other than those tested can also be used.

TABLE 3

Growth Optimization of Eleven Species.

| Species | Optimum Media |
|---|---|
| *Arabidopsis thaliana* | 1/2 × Hoaglands or 1/2 × MS |
| *Asrostis stolonifera* | All media |
| *Browallia speciosa* | 1/2 × Hoaglands, DMG, Arabidopsis |
| *Coleus blumei* | All media |
| *Digitalis purpurea* | 1/2 × MS, 1/2 × Hoaglands, DMG |
| *Digitaria sanguinalis* | All media |
| *Eragrostis curbula* | All media |
| *Inula ensifolia* | All media |
| *Nicotiana tabacum* | 1/2 × Hoaglands or 1/2 × MS |
| *Panicum coloratum* | 1/2 × MS |
| *Petunia hybrida* | All media |

Environmental Conditions for Microscreen

In order to have vigorous and uniform growth of the plants in the microscreen, suitable environmental conditions are required. Among the important conditions are temperature, photoperiod, quantity of light, humidity and $CO_2$ concentration. Temperature, photoperiod and light level were not systematically studied; the following values were found to be suitable based on prior experience with one or more of the selected species:

| | |
|---|---|
| temperature: | 25–28° C. |
| photoperiod: | 14–16 h |
| light level: | 45–80 umol/m2/s PAR. |

It was found that humidity surrounding the microtiter plates must be kept high enough to prevent the evaporation of water from the agar in the microtiter wells. A humidity level between 80% and 100% was suitable.

An important environmental parameter affecting both plant vigor and uniformity was found to be the $CO_2$ concentration in the atmosphere surrounding the microtiter plate. Preliminary experiments with 68 species indicated that 58% showed improved growth when the atmosphere surrounding the plates was supplemented to about 10,000 ppm $CO_2$ compared to growth at ambient $CO_2$ concentration.

To further document this effect and to determine more precisely the optimal $CO_2$ levels, microscreen plates were incubated in atmospheres containing varying amounts of $CO_2$. Six identical growth chambers were constructed that allowed the level of $CO_2$ that surrounded the microtiter dishes to be controlled. These chambers were constructed of clear plexiglass and were sealed, except for inlet and outlet ports, when the lids were attached. Flow meters and valves were used to mix pure $CO_2$ with air to produce gas mixtures containing air (21% oxygen, 79% nitrogen) plus varying concentrations of $CO_2$. These gas mixtures were continuously passed through the plexiglass chambers to ensure a constant $CO_2$ environment. Sampling ports built into the chambers were used to periodically remove 1 mL gas samples. The $CO_2$ content of these samples was determined using a gas chromatograph with known $CO_2$ standards for calibration. Total flow rate through these 34.3×14.6×36.8 cm (18,429 $cm^3$ total volume) chambers was between 4250 and 9440 $cm^3$/min. Gas mixtures were humidified by bubbling through water baths within the chambers, resulting in internal humidities ranging from 75 to 95% relative humidity. Temperature was maintained between 25° C. and 29° C. Light levels were between 45 and 66 umol/m2/s PAR and the photoperiod was 14 h. The light, temperature and humidity levels were similar in all 6 chambers.

Microtiter dishes containing no herbicides were prepared as described, and placed into the plexiglass chambers for 12 days (7 days for crabgrass). At that time, the dishes were removed and assayed for chlorophyll content as described below. Quantitative results are expressed as the mean and coefficient of variability of the chlorophyll content per seedling for a set of 32–48 plants of a single species in a single $CO_2$ concentration. The results of one experiment are shown in FIG. 1. Other, independent experiments (not shown) confirmed the conclusions of this experiment.

FIGS. 1A–1F show the effects of varying concentrations of $CO_2$ surrounding the microtiter dishes on the growth of seven different species (*Nicotiana tabacum, Browallia speciosa, Oxalis stricta, petunia hybrida, Coleus blumei, Digitaria sanguinalis,* and *Arabidopsis thaliana*) used in the microscreen. In all cases, the lowest $CO_2$ concentration tested is that derived from ambient air without supplemental $CO_2$. (Note that the amount of $CO_2$ in ambient air varies, depending on, for example, the season and weather; in this experiment ambient $CO_2$ concentration was 550 ppm.)

In order for the microscreen to be useful, growth of plants used in the assay needs to be both vigorous and uniform. Because of this dual requirement, both the mean size of the plants and the variability between plants (coefficient of variation) are plotted in FIGS. 1A–1F. In general, the mean and the coefficient of variation are inversely related to each other such that conditions which give small plants generally also have highly variable plant sizes and conditions which give vigorous plants generally have lower variability.

Of the seven species tested, most show a strong dependence of growth on $CO_2$ concentration. Thus, *Arabidopsis thaliana, Browallia speciosa, Coleus blumei, Nicotiana tabacum* and *petunia hybrida* show less than optimum growth at ambient $CO_2$ and much improved growth as the $CO_2$ level is increased. Improved growth for *Arabidposis thaliana, Petunia hybrida, Browallia speciosa, Coleus blumei* and *Nicotiana tabacum,* as determined by increased chlorophyll content and reduced coefficient of variation, was observed at 2200 ppm $CO_2$, and optimum growth was observed between 5000 and 10,000 ppm $CO_2$. At higher $CO_2$ concentrations, growth of most of these 5 species was partially inhibited. The two other species tested either showed no strong effect of $CO_2$ level on growth (*Digitaria sanguinalis*) or an inconsistent response from one experiment to the next (*Oxalis stricta*). Thus, for 5 of the 7 species tested, supplemental $CO_2$ ranging from 5000–20,000 ppm, preferably about 10,000 ppm, was demonstrated to produce plants which were sufficiently vigorous and uniform for the microscreen. For the other 2 plants tested, supplemental $CO_2$ was not required, but it was not detrimental to their growth.

It is believed that the improvement in growth of the plants by the $CO_2$ supplementation in the atmosphere surrounding the microtiter plates is caused by a resulting increase in the $CO_2$ in the micro-environment within the wells of the microtiter plate. Poor growth of many of the plants in the absence of elevated $CO_2$ may be caused by a decrease in the $CO_2$ level inside the microtiter dishes. Although these dishes are not sealed, their lids do fit relatively tightly, thus producing a partial barrier to diffusion of gases in and out of the dishes. If the plants take up $CO_2$ by photosynthesis at a fast enough rate inside the dishes, the level of $CO_2$ may fall below the level necessary to support an optimum level of photosynthesis. By placing the dishes in elevated $CO_2$ atmospheres, there is a higher initial level of $CO_2$ inside the plates to support photosynthetic growth. More importantly, as the $CO_2$ level inside the plates is reduced by photosynthesis, the rate of diffusion of $CO_2$ into the plates will be increased because of the larger difference in $CO_2$ levels between the external and internal atmospheres.

On the other hand, it is possible that the improvement caused by elevated $CO_2$ atmospheres is due to other effects of the $CO_2$. Possible mechanisms for this effect could be the effect of $CO_2$ on ethylene or other hormone systems or the effect of $CO_2$ on the pH of the media. In any case, it is clear that elevated $CO_2$ levels are important for obtaining vigorous and uniform growth of most species of plants in the microscreen assay.

It is apparent that the whole plant herbicide microscreen requires specialized incubation conditions that cannot be achieved using a standard laboratory incubator. Most of the plants favor elevated $CO_2$ concentrations (5000–20,000 ppm) which can be achieved by installing a $CO_2$ monitor wherein $CO_2$ levels can be carefully controlled. High relative humidity (85–90%) is also important so that the agarose in the microwells does not dry out before the end of the 14 day growth period. Most standard incubators cannot reach this level of humidity. In addition, most standard incubators have lights mounted on the bottom of each shelf, a configuration that causes the formation of a condensate on the lids of the microtiter plates. Heat from the lights causes water to evaporate and then condense on the cooler lids. As a result, plants cannot be rated for injury without first removing the condensate because the condensate distorts the view into the plates. This problem can be solved by insulating the space between the lights and the shelf. Percival Scientific Inc., Model CU-32L tissue culture chamber offers a suitable configuration. Moreover, the lights in this incubator are arranged in a "tic tac toe" pattern that results in more uniform lighting in the incubator. In addition, air is circulated across each shelf to give more even temperature and humidity control. This incubator can be modified by installing a $CO_2$ monitor, as well as a modified humidifier which can achieve humidities up to 92%.

Seed Germination

Uniform seed germination is required in order to maximize the utility of a whole plant herbicide microscreen assay. Accordingly, seed germination was evaluated under a variety of seed pretreatment protocols. *Browallia speciosa, Coleus blumei, Digitalis purpurea, Digitaria sanguinalis, Nicotiana tabacum, Oxalis stricta* and *Petunia hybrida* seeds were treated in five different ways prior to planting (ethanol, acid, bleach, UV sterilization and cold). A small amount of each seed was placed in a 1.5 mL micro centrifuge tube and treated with ethanol, acid or bleach as described below. One milliliter of 0.3 M ethanol in deionized water was added to seeds and seeds were soaked for 24 h (Taylorson, R. B. *Weed Science* (1989) 37, 93–97). One milliliter of 6 M sulfuric acid was added to seeds and the tube was shaken for 1 min. Then the seeds were soaked for 15 min and rinsed 5 times with deionized water (Brecke, B. J. and Duke, W. B. *Weed Science* (1980) 28(6), 683–695). One milliliter of 25% bleach (125 mL Clorox, 375 mL deionized water, 10 drops of Triton™ X-100 (Sigma Chemical Co., St. Louis, Mo.) was added to seeds and the tube was shaken for 2 min. The seeds were soaked for 7 min, then rinsed 5 times with deionized water. For all seed treatments, the wet seeds were transferred to a petri dish containing filter paper and the seeds were allowed to dry overnight.

Seeds were also UV sterilized by placing seeds on top of a UV light box in a sterile hood which was also illuminated with a UV lamp from above. Seeds were exposed to the UV lights for 16 h. For cold treatment, seeds were planted in agarose in 96-well microtiter plates and placed in a refrigerator at 4° C. for 24 h.

Plates were prepared as described above with one microtiter plate containing seed from one plant species which received one seed treatment. Plants were visually evaluated at 14 DAP. The results for each tested plant species are presented below.

Browallia: Browallia had 100% germination for all treatments. The acid treatment was unacceptable because the plants were very uneven in growth and had poor growth in general. The UV and bleach treatments both had a few malformed plants, so these treatments were of questionable use. Plants under cold treatment were slightly smaller than controls but otherwise these plants were similar to controls. The ethanol treated plants were also similar to controls but slightly less uniform. Controls appeared to be the best plants. Therefore, no seed treatments were necessary for growth of Browallia in microtiter plates.

Coleus: The germination rate for all treatments of Coleus was excellent (98–100%). Control (untreated) Coleus looked excellent and grew very uniformly with a good green color. Bleach and ethanol treatments looked similar to controls. The acid treatment was somewhat uneven and showed some bleaching. The UV treated plants were slightly less uniform than controls and the cold treated plants were smaller than controls. Control plants looked best; no seed treatments were necessary for growth of Coleus in microtiter plates.

Digitalis: The bleach treatment was best for Digitalis with 100% germination compared to 83% germination with controls. Bleach treated plants were also more uniform than controls. With all treatments however, under the optimized conditions of this test, the Digitalis plants were too large for the plates and were therefore eliminated from further consideration.

Digitaria: The germination rate of Digitaria varied depending on type of seed treatment. Control (untreated) Digitaria had 96% germination, were fairly uniform in growth and had a pale green color. Bleach treated plants had 85% germination, were stunted and were less uniform in growth than control (untreated plants). The bleach treatment was unacceptable. The acid treated plants had 92% germination and were slightly less uniform in growth than controls. UV treated plants looked similar to controls and had 96% germination. Cold treated plants were slightly larger than controls and had 94% germination. Ethanol treated plants had the highest germination rate (98%) and looked similar to controls except for some slight bleaching. Overall the controls were the best looking plants. Therefore, no seed treatments were necessary for growth of crabgrass in microtiter plates.

Nicotiana: For all treatments, the germination rate for Nicotiana was 96–98% and no differences were observed in growth/uniformity from the control (untreated) Nicotiana. The control Nicotiana was very uniform with 4 leaves and very erect plants with a deep green color. No seed treatments were necessary for growth of Nicotiana in microtiter plates.

Oxalis: The acid treatment was unacceptable for Oxalis since no seeds germinated. The UV and bleach treated plants showed some bleaching and were more uneven in growth compared to controls, so these treatments were eliminated. The germination rate for ethanol treated plants was slightly lower than controls, 88% for ethanol compared to 92% for controls and the plants were more uneven in growth. The cold treated plants, however had a slightly higher germination rate than controls, 94 and 92%, respectively and were slightly more uniform in growth. The cold treatment was selected as the method of choice for growing Oxalis in microtiter plates.

Petunia: The germination rate was excellent (98–100%) for all treatments of Petunia, but there were differences in growth uniformity and appearance. The control (untreated) Petunia were pale green and uneven in growth and were not ideal for use in the microscreen. The cold treated plants were very uneven in growth and were found to be unacceptable. Bleach treated Petunia showed a bleached appearance and were also not acceptable. The UV and ethanol treated plants looked slightly better than controls (more uniform in growth). The acid treated Petunia had 100% germination and the plants were larger, fairly uniform in growth and a good color. The acid treatment was selected as the best method for growing Petunia in microtiter plates.

Assay Automation

Solubilization of compounds: Tests were conducted to determine the maximum amount of DMSO each plant species would tolerate. DMSO was selected as the universal solvent for solubilizing compounds into aqueous media because it is polar, less volatile than other organic solvents and is an excellent solvent for most smaller organic molecules. In order to determine the maximum concentration that each species could tolerate, DMSO was added to ½×MS media and mixed with agarose to yield 0, 0.1, 0.3, 0.6, and 1.0% DMSO solutions. One seed was planted in each well with 32 wells per species. Injury was evaluated relative to control (untreated) plants. The following ten species were tested: *Arabidopsis thaliana, Browallia speicosa, Coleus blumei, Digitaria sanguinalis, Eragrostis curbula, Inula ensifolia, Nicotiana tabacum, Oxalis stricta, Panicum coloratum* and *Petunia hybrida*. Plants were evaluated for injury 14 DAP. The following observations were made:

Arabidopsis: No injury was observed at the highest concentration of DMSO tested (1.0%).

Browallia: No injury was observed at the highest concentration of DMSO tested (1.0%).

Coleus: No injury was observed at the highest concentration of DMSO tested (1.0%).

Digitaria: No injury was observed at 0.1% DMSO. At 0.3 to 1.0% DMSO there was slightly more bronzing of the newest leaf.

Eragrostis: No injury was observed up to 0.3% DMSO, but at 0.6 and 1.0% DMSO there was bronzing/burning of leaf tips.

Inula: DMSO improved germination, growth uniformity and greenness. Plants treated at 1.0% DMSO appeared to be the most healthy.

Nicotiana: No injury was observed at the highest concentration of DMSO tested (1.0%).

Oxalis: No injury was observed up to 0.3% DMSO. The plants had a poor appearance at 0.6% DMSO and germination dropped by 45% at 1% DMSO.

Panicum: No injury was observed up to 0.3% DMSO, but at 0.6 and 1.0% DMSO, the plants were slightly chlorotic at the leaf tips.

Petunia: No injury was observed up to 0.3% DMSO. At 0.6 and 1.0% DMSO, slight injury was observed.

Digitaria was most sensitive to DMSO and thus dictated the concentration to be used for solubilization of compounds. Based on results with Digitaria, the concentration of DMSO used was 0.1%.

Automation of Plate Preparation: Five milligrams of each compound were weighed into deep well microtiter plates, 88 compounds per plate with the first column empty (column 1) for controls. Using a Tomtec Quadra-96™ pipettor, 500 uL of DMSO were pipetted into each well to prepare a 10,000 ppm compound solution. A lid was placed on each plate, sealing each well and each plate was tumbled for 10 min to solubilize the compounds. Each plate was centrifuged for 15 seconds to remove DMSO from the lids. These plates were the mother plates. Daughter plates were prepared from mother plates by pipetting 425 uL of ½×MS media into each well of the daughter plate (1.2 mL deep well plate) using the Quadra-96™. This step was repeated. Then 147 uL of ½×MS media was drawn into pipette tips plus 3 uL of DMSO from the mother plate and dispensed into daughter plate with mixing. Using the Quadra-96™, treatment plates were prepared by drawing 250 uL from the daughter plate (30 ppm compound solution) and dispensing 33 uL into each well of 4 standard microtiter plates. Using the Quadra-96™, 400 uL 0.6% agarose were drawn into pipette tips and 66 uL were dispensed into each well of the 4 treatment plates (standard microtiter plates) yielding a 10 ppm compound solution in 0.4% agarose. No additional mixing steps were necessary for mixing of the agarose and ½×MS media/compound solutions. A total of 16 treatment plates were prepared from each mother plate to accommodate 7 species (1 species per plate) and duplicate tests (2 plates were discarded).

Automation of Seeding

One seed of each species is planted manually in each well using a forceps. In addition, several methods for automation of seed dispensing are possible. Several methods of automating the seeding have been tested with the goal of placing one seed in each well of a 96-well microtiter plate.

A template seeder was designed by Berry Seeder Co. (Elizabeth City, N.C.) for seeding into 96-well microtiter plates. This seeder has stainless steel plates with 96 holes which are in alignment with the microtiter plate wells. There were 4 stainless steel plates, each with different diameter holes to accommodate the different sized seeds. Each stainless steel plate is attached to a plexiglass box containing a vacuum line. High pressure air was run into a separate valve in the box and opening the valve resulted in vibration of the stainless steel plate. Seeds were placed on the stainless steel plates with the vacuum running and the high pressure air valve opened to vibrate excess seeds out of each hole. Experiments were run with *Arabidopsis thaliana, Browallia speciosa, Coleus blumei, Digitalis purpurea, Digitaria sanguinalis, Nicotiana tabacum* and *Petunia hybrida*. The Berry template seeder worked well with Browallia and Coleus seeds with 90–95% singulation. These seeds are quite round and were the largest seeds tested (0.040" diameter for Coleus and 0.035" diameter for Browallia). Digitaria, which is an elongated seed, could not be singulated because it would not stick in the holes (holes were too small). With Petunia and Digitalis seeds, the holes in the stainless steel plates were either too large (seeds were pulled through the holes) or too small (seeds would not stick). Arabidopsis seeds had multiple seeds in many of the holes. Nicotiana seeds had 26–45% singulation with the remainder being either multiple seeds or no seeds (seeds would be pulled through the holes). Although the Berry template seeder had high singulation of the Coleus and Browallia seeds, the seeder is quite temperamental. It takes some "tweaking" to attain this level of singulation. This seeder did not work well with the other seeds. Based on these tests, this seeder would not work for automation of seeding.

A needle seeder (Seed-Air-Matic™, KW Engineering Pty. Ltd., Queensland, Australia) for seeding into plug trays has been tested to determine the feasibility of using with the following seeds: Arabidopsis, Browallia, Coleus, Digitaria, Nicotiana, Oxalis and Petunia. This seeder has 8–20 syringe needles of varying bore sizes that were connected to vacuum. Seeds were placed in a hopper that vibrates. The needles dipped into the hopper, picked up individual seeds and dropped the seeds into guide tubes, which in turn released into plug trays using a short burst of high pressure air. A row of seeds was picked up and dropped in 1–4 seconds. The KW Engineering seeder was used to test singulation of Arabidopsis, Browallia, Coleus, Digitaria, Nicotiana, Oxalis and Petunia seeds into 96-well microtiter plates. This seeder has been modified to seed into microtiter plate format. Browallia, Coleus, Digitaria, Nicotiana, Oxalis and Petunia seeds had 90–96% singulation using a single needle. Arabidopsis singulation rate was about 83–85%. Individual vacuum regulators have been installed to achieve these levels of singulation with multiple needles (8–12). At these singulation rates, missed or multiple seeded wells can be corrected manually.

Batching Systems (Owings, Md.) uses a vibratory bowl to singulate parts (nuts, bolts, game pieces, etc.) and an optical eye to count the parts. For use as a seeder specifically for seeding into 96- or 48-well microtiter plates, seeds would be placed in a vibratory bowl and would "walk" up a ramp. At the end of the ramp, the width would be adjusted so that only one seed at a time could fit on the ramp. The seeds would drop down and be counted by a dual-view optics system. A microtiter plate would be placed on an X-Y table to singulate seeds.

A preferred method of seeding comprises a combination of elements making up a seed dispensing system that features a seed pick and place mechanism for a plurality of containers, a seed placement monitoring device for a plurality of containers, and a control system to inform the operator of the location of potentially misplaced seeds or to provide feedback for automatic re-seeding of any missed containers. Alternatively, a discrete correction station may be a component of the system. A preferred embodiment includes in the pick and place mechanism the feature of individual control of vacuum to individual seed holding tubes (or needles). This individual control of vacuum combined with the seed pickup tube design improves the reliability for single seed pickup. Additional features of the preferred method include the proper positioning of tip of each seed holding tube during seed pickup and during seed deposition, and providing in each container a substance that when contacted with the seed will inhibit or prevent further movement of the seed within the container and inhibit or prevent the seed from being expelled from the container due to air currents and/or static charge.

FIG. 4 shows the schematics of the basic elements of an automated system for placing seeds into wells of a plurality of microtiter plates, monitoring the accuracy of placement, and correcting for errors. The system will also work to place insect eggs into microwells so as to enable an automated insecticide micro-assay, although the system will be described in the context of handling seeds for an automated herbicide micro-assay. A control device 20 is connected to a seed handling and monitoring device 22 and a seed correcting station 24. The seed handling and monitoring device consists of a base 26 covered by an enclosure 28 which may be supplied with positive pressure filtered air by air supply device 30 or may be provided with negative pressure to control volatile organic compounds. Access door 32 allows access for placing seeds in a seed supply station 34, and access door 36 allows access for loading and unloading a plate carrier 38 with a plurality of microtiter plates, such as plate 40. Within the enclosure is a transport mechanism 42 for transporting an overhead module 46 that contains a monitoring camera 48, a seed holder 50 and a plate identification reader 52.

Figure 5A:
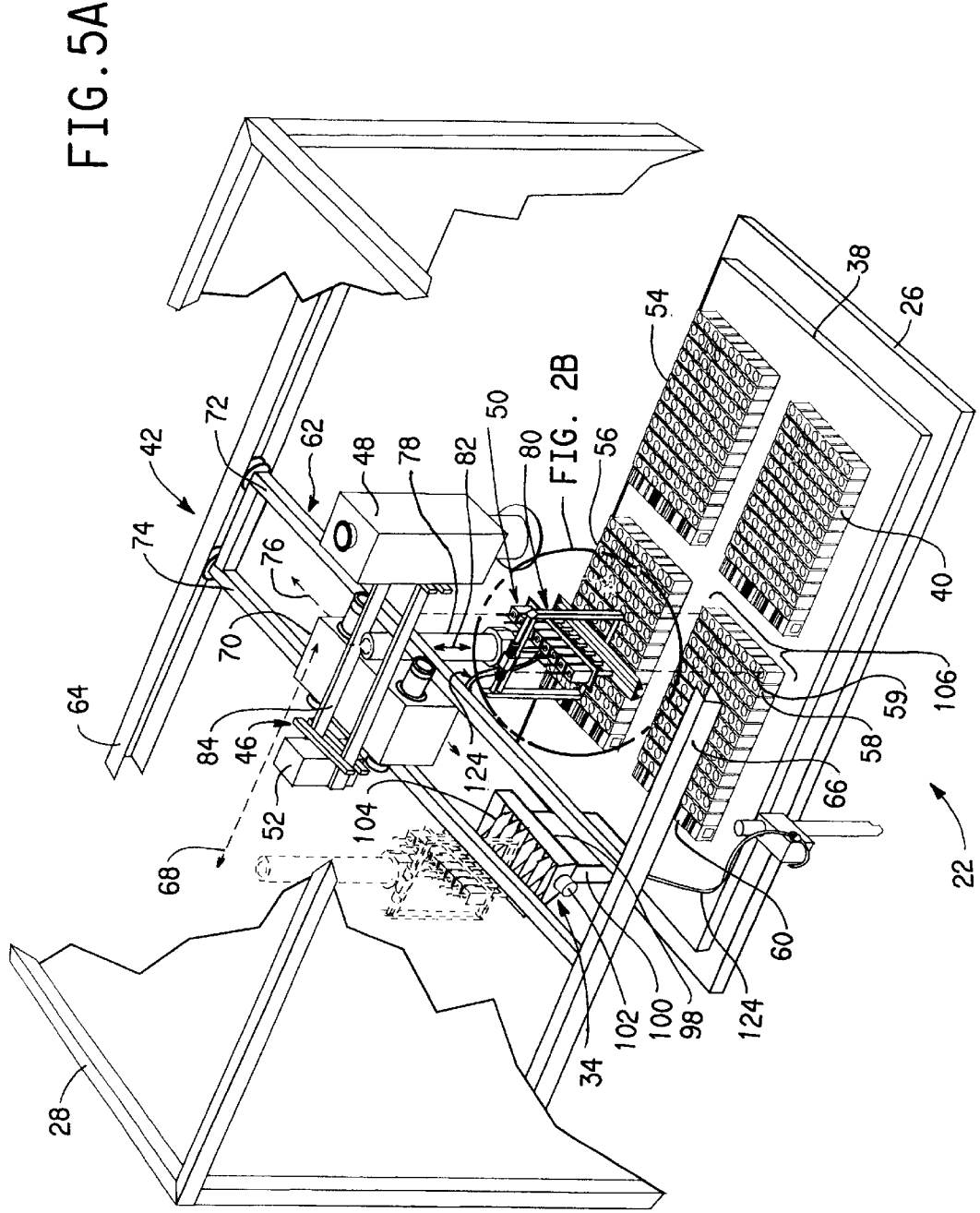
FIG. 5A is an isometric view of the seed handling and monitoring system.
Figure 5B:
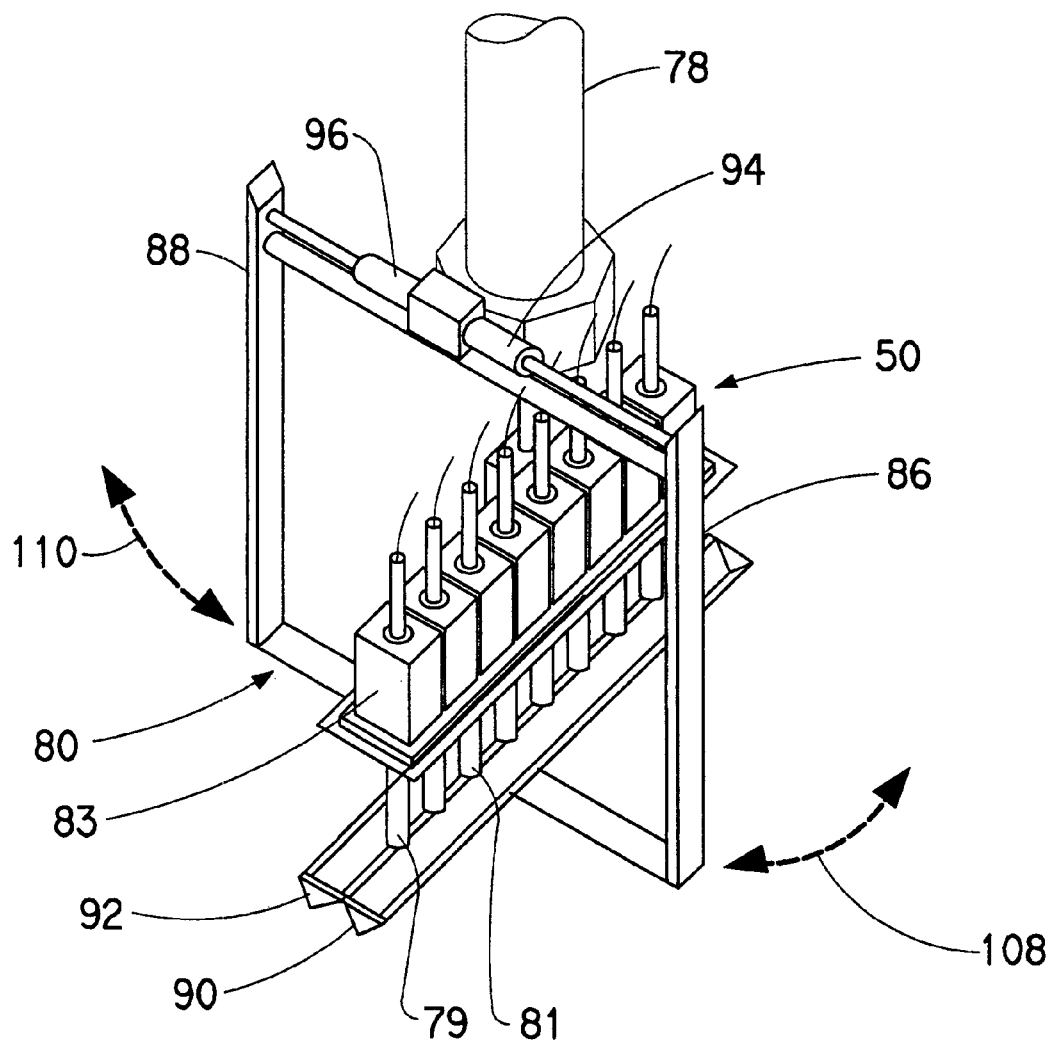
FIG. 5B is a break away of a portion of the seed handling system.

FIG. 5A shows an detailed view of the seed handling and monitoring device 22, and FIG. 5B shows a break away of a portion of the seed handling system. The base 26 supports the removable plate carrier 38 that is shown with a plurality (4) of microtiter plates 40, 54, 56, and 58 in predetermined locations. The microtiter plates are of the size that contain 96 wells, such as well 59 in plate 58, in a 12×8 array and each plate has a bar code label, such as label 60 on plate 58, preferably on the top surface of the plate. Plates having different dimensions and different numbers and configurations of wells can also be used by making appropriate changes in the seed holder 50. Within each well is a premeasured volume (not shown) of a compound to be tested and a plant growth medium, which can also contain agar. There may be a different compound in each well and several control wells in each plate. Different plates may contain the same compounds to check reproducibility. The carrier can be configured to hold more or less than the illustrated 4 plates. The carrier may be placed on the base either manually, as described via door 36, after removing a lid (not shown) from each plate, or the carrier may be placed automatically from an autofeeder that may hold up to 15 carriers and may include a lid handling feature.

The transport mechanism 42 consists of an overhead X-Y positioning system for overhead module 46, the mechanism comprising a first carriage 62 that runs on rails 64 and 66 for positioning the module in the X-direction indicated by arrows 68; and a second carriage 70 that runs on rails 72 and 74 for positioning the module in the Y-direction indicated by arrows 76. Attached to the carriage 70 is the overhead module 46 that comprises actuator 78, seed holder 50, monitoring camera 48, plate identification reader 52, and seed catcher 80. Actuator 78 mounted on module 46 is for positioning the seed holder 50 in the Z-direction indicated by arrows 82. Elements making up module 46 may be attached to a module frame 84 as shown, or they may be attached directly to carriage 70. The seed holder 50 (FIG. 5B) comprises a plurality of seed pickup tubes, such as tube 79 and tube 81 that extend from tube block 83. The seed catcher 80 is attached to actuator 78 and comprises two moveable arms 86 and 88 that support angled bars 90 and 92 respectively that are underneath the ends of the plurality of seed pickup tubes when they are in the upper Z-direction. Actuators 94 and 96 control the motion of arms 86 and 88 respectively.

The seed supply station 34 consists of a seed trough 98 for holding a supply of seeds, a frame 100 resiliently supporting the trough, and a vibrator 102 attached to the trough for vibrating it to cause the seeds to be fluidized or air-borne in the trough. The trough may contain dividers, such as divider 104 to keep the seeds contained in individual compartments in line with individual seed pickup tubes during pickup by seed holder 50. The trough and dividers are preferably made from a conductive material, such as stainless steel or a filled conductive polymer, that can be grounded to prevent static electricity buildup. The seed supply station may be located in a central position to minimize travel distance to all the wells.

In FIG. 5A, the transport mechanism 42 is shown in a position to permit insertion of seeds in a row of wells, such as well 59 in row 106 in plate 58. In this position, plate identification reader 52, also known as a bar code reader, has passed over bar code 60 and identified plate 58 to the control device 20 (FIG. 4). There are position encoders (not shown) on the X and Y carriages so the controller 20 can confirm which row of wells the seed holder is positioned over. The seed catcher 80 is in a closed position as shown to catch any seeds that may be dislodged during transport of the seeds from the supply station 34 to the row of wells 106. If a seed were to be dislodged, it would fall into one of the angled bars 90 or 92 instead of landing in one of the wells being crossed during transport, which would result in a seeding error that may not be detected. Periodically, the bars 90 and 92 would be emptied of fallen seeds. Before the seed holder can proceed in the Z-direction to place the seeds in a row of wells, the seed catcher must be in an open position with the arms 86 and 88 moved in the direction of arrows 108 and 110 respectively. This will allow the tube block 83 to pass between bar 90 and bar 92 so that the tips of tubes, such as 79 and 81 can enter the wells, such as 59, in row 106 and deposit in each well of row 106 a seed held by each tube. After deposit of the seeds, the tube block would be retracted in the Z-direction and the transport mechanism 42 would move to place camera 48 over row 106 so each well in row 106 could be monitored for the presence or absence of seeds. The camera 48 is positioned far enough above the wells that its field of view includes all 8 wells in row 106 and the wells are shallow enough at that position so the image of the outermost wells still enables the camera to see the bottom of the well where the seed is deposited. By "bottom of the well" is meant the top surface of the plant growth medium containing compound that is placed in the well and is the surface on which the seed will rest. Typically, in a 10 mm deep well there may be about a 4 mm deep layer of plant growth medium containing compound so the "bottom of the well" is about 6 mm down from the top of the well.

Seed holder 50 is shown with a linear array of 8 tubes, such as 79 and 81, in block 83. This could alternatively be a rectangular array of tubes, such as 4×2 or 4×4 array, or any other similar arrangement. A more compact array may have an advantage to make monitoring of the wells by camera 48 more reliable by minimizing any parallax optical problems or allowing the camera to be located closer to the wells.

Figure 6:
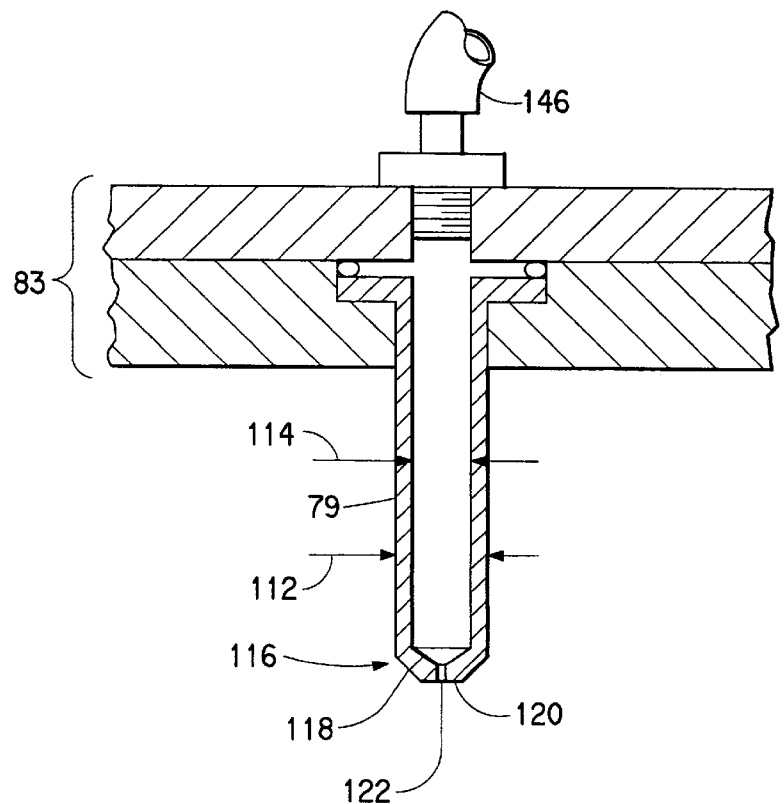
FIG. 6 is a section view of a seed pickup tube.

Referring to FIG. 6, which is an enlarged section view of tube 79, the tube has a relatively large outer diameter 112 of about 1–4 mm, preferably about 3.0 mm to resist bending and enable accurate positioning in the well. Throughout most of the length of tube 79 there is an enlarged bore 114 of 0.5–3 mm, preferably of about 1.5 mm that terminates near the tip 116. The tip may have a chamfer 118 to present a small flat end 120 to the seeds and deflect adjacent seeds, in motion in a fluidized bed of seeds, away from the single one held at the flat end. A relatively small diameter hole 122 extends from the end of bore 114 through the tip 116 for fluid communication with a single seed. The size of the hold is approximately proportional to the size of the seed. Conveniently, the hole will be circular in cross-section and the diameter of the hole may be smaller than smallest dimension of the seed. For unusually small seeds, this hole 122 may have a diameter of only 0.05 mm. Bore 114 is in communication with a source of air that alternately may be under vacuum or pressure. The pressure can be useful to clear any debris from the hole 122 and to dislodge the seed. To eliminate problems with static electricity near very small lightweight seeds, tube 79, which is representative of all tubes, is made of a conductive material which is corrosion-resistant, such as 304 stainless steel, and is grounded via the block 83, which also conductive, and a grounding cable 124 (FIG. 5A) or other suitable grounding means.

Figure 7:
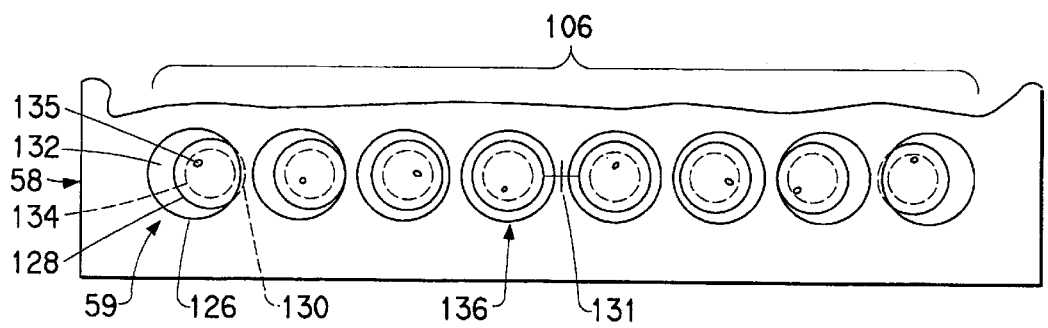
FIG. 7 is an enlarged view of a row of wells in a microtiter plate as seen by a monitoring camera.

The camera 48 is arranged above the wells at a distance sufficient to obtain a clear high resolution view of the bottom of the wells. FIG. 7 illustrates an enlarged perspective view of what the camera sees looking at the row 106 of wells. Circle 126 represents the top of well 59, circle 128 represents the bottom of the well that is a slightly smaller diameter than the top circle 126. Typically, the top surface of plant growth medium containing compound mix will define the visual bottom of the well. Part of the very edge of bottom circle 128 may be partially blocked from view by top circle 126 as is shown at 130. This is due to parallax which is an apparent shift in position of the bottom circle relative to the top circle due to the actual line of sight from the camera center 131 to the well, which is different for each well. Surface 132 represents the sidewall of well 59 that connects the top circle to the bottom circle. Dashed circle 134 represents the target circle for a seed, such as seed 135, placed at the bottom of the well. It is a smaller diameter circle than bottom circle 128 so the seed will be spaced away from the sidewall surface 132. In other wells, such as well 136 near the center of row 106, there may not be any blocking of the bottom circle by the top circle. In the view of FIG. 7, the camera can see the entire area of the target circle for all wells. This is important so the camera can notify the control system if the seeds have been successfully placed in the target circle of each well. Based on the camera view, the control system can make several determinations about each seeded well:

1) one seed in the target circle only;
2) no seed in the target circle and no seed in the well;
3) no seed in the target circle and one seed in the well;
4) more than one seed in the well, which may be in or out of the target circle.

A seed that falls at the corner where the bottom circle meets the sidewall may not be seen due to the poor contrast at the corner; and a seed that falls in a blocked area like 130 may not be seen. In such circumstances, there may be a small degree of uncertainty about the determinations. It is expected that such circumstances will be rare due to the accuracy and reliability of the seed placement system. Ideally, such uncertainty is avoided by use of multiple cameras looking at a row or a single camera indexing over two viewing positions, each with fewer wells, to eliminate any parallax problem. Using shallower microtiter wells may also eliminate any parallax problem. The microtiter plates are backlighted to give good lighting and contrast at the bottom of the well for the camera.

Figure 8:
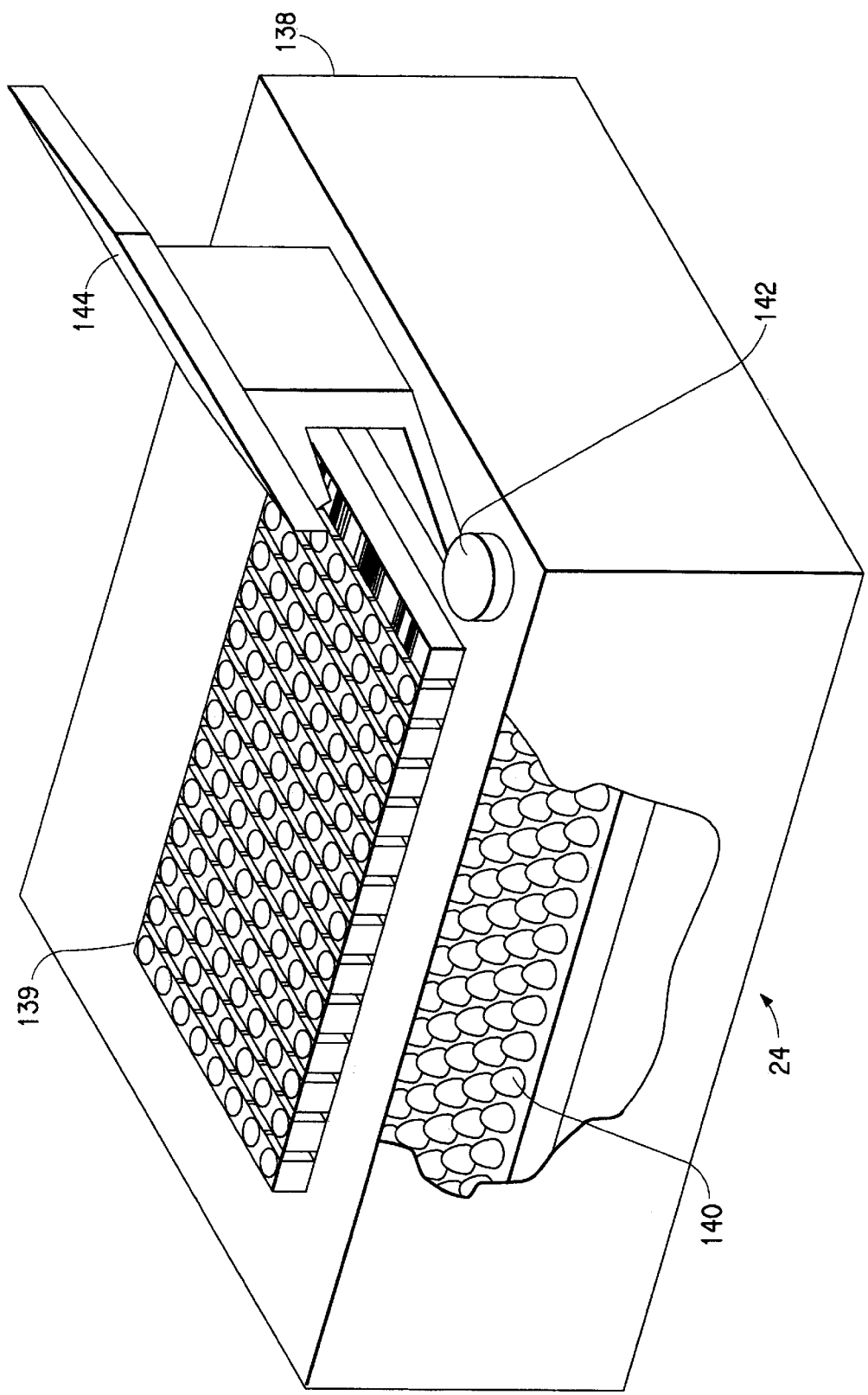
FIG. 8 is an isometric view of the well illumination and correction station.

If determination #1 is made for all just-seeded wells, the control system can tell the transport mechanism to go get seeds for the next row of wells. If determination #2 is made for any well of the just-seeded wells, the control system can tell the transport mechanism to go get a seed for the particular well that is missing a seed in the target area. If determination #2 persists for the same cell after an attempted correction, the control system can create an error data file to alert the operator that a #2 defect exists for this particular well. If determination #3 is made for any well of the just-seeded wells, the control system can create an error data file to alert the operator that a defect #3 exists for a particular well. If determination #4 is made for any well of the just-seeded wells, the control system can create an error data file to alert the operator that a defect #4 exists for a particular well. The error data file can be used to alert the operator to make manual corrections. In an alternate embodiment, the seed correcting station 24, referring to FIGS. 4 and 8, is a manually operated/machine assisted station where an operator can place a microtiter plate and examine and correct for determinations #2, 3, and 4 as identified by the camera and control system. It consists of a plate holder 138 that supports a barcoded microtiter plate 139 that a barcode scanner 144 can read. This allows the control device 20 to identify a particular plate. The microtiter plate 139 is over an LED array 140 located within the holder as seen in the cutaway view of FIG. 8. The LED array 140 consists of an illuminating LED positioned under each well of the microtiter plate, which in the case shown would be an 8×12 array of 96 LEDs. The control device 20 can independently illuminate particular LEDs by accessing error data files to locate the wells with the #2, 3, and 4 determinations based on the earlier examination of that plate by the monitoring camera 48. The operator can then take the corrective action for each illuminated well. Descriminations between determinations can be made if desired by the manner in which the LED is illuminated, i.e., continuously illuminated, blinking slowly, blinking quickly, etc. The station 24 also has an input switch 142 to permit communication with the control device 20 to turn off selected LEDs, and indicate manual correction has occurred.

Figure 9:
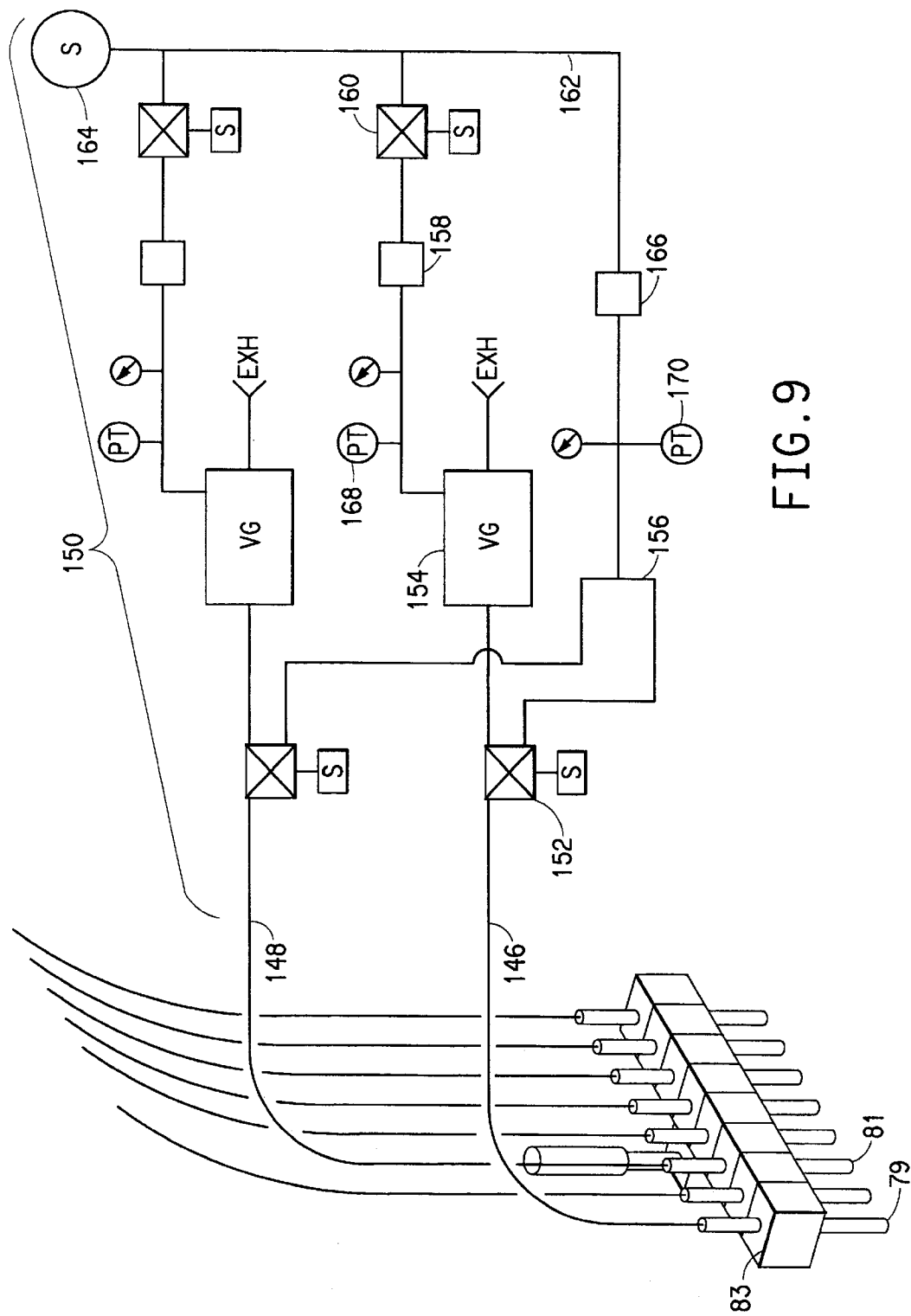
FIG. 9 is a partial schematic illustration of pneumatics for the seed pickup tubes.

Part of the seed holder 50 is a pneumatic system for controlling the seed pickup and drop off function as seen referring to FIGS. 9 and 6. Referring to FIG. 9, each seed pickup tube, such as tube 79 or 81 in tube block 83, is in fluid communication via conduits 146 and 148, respectively, with pneumatic system 150. This system will be described referring to tube 79 and is understood to be the same for other seed pickup tubes. Conduit 146 is connected to a solenoid operated, three-way, selector valve 152 which is connected to a vacuum generator 154 and a pressure manifold 156. The vacuum generator produces vacuum by a venturi effect and is connected to a pressure regulator 158 and a solenoid operated, two way, selector valve 160, and a pressure manifold 162. The pressure manifold 162 is connected to a source of pressure 164. Pressure manifold 156 is connected to a pressure regulator 166 which is connected to pressure manifold 162. The system allows individual vacuum adjustment to each seed pickup tube for the purpose of 1) adjusting to individual tolerances in the small seed pickup hole, such as hole 122 in tube 79 (FIG. 6), and 2) individually turning "on" the vacuum in one or more tubes while it remains "off" in the remaining tubes. The individual vacuum level, or flow, for a tube is individually triggered by actuating the selector valve 160 to direct pressure to the vacuum generator, and then adjusting the pressure regulator 158 to achieve the desired vacuum level. The individual adjustment would be done by trial and error by observing the seed pickup performance for that tube. Alternatively, for automated monitoring of the pneumatic system, there is a pressure transducer 168 between the regulator 158 and vacuum generator 154, and a pressure transducer 170 between pressure regulator 166 and pressure manifold 156. The transducer, such as 168 for each seed pickup tube, and transducer 170 are connected electrically to the control device 20 for continuous monitoring.

During continuous automated operation, the seed handling and monitoring system works as follows referring to FIGS. 4, 5A, 5B, 6, 8 and 9. Beginning at the position shown in FIG. 5A, the operator has already loaded the seeds in the seed supply station 34 and has loaded carrier 38 with microtiter plates 40, 54, 56 and 58 that are prepared with plant growth medium and a different compound for testing in each well, such as well 50. The operator removes the lids from the plates and places the carrier 38 in the enclosure 28 and makes sure the air supply/suction device 30 is providing a steady flow of filtered air/negative pressure to the enclosure. The operator closes the doors 32 and 36. This minimizes the chance of airborne contamination and controls any air currents that may tend to dislodge seeds during handling. The seed holder 50, as shown in FIG. 5B, has already successfully picked up seeds from seed supply station 34 and is positioned over row 106 in preparation for depositing seeds in the wells of row 106.

Automated operation, illustrating reseeding, proceeds as follows:

valves, such as 160 and 152, remain actuated to maintain vacuum (produced by the vacuum generator 154) and hold a single seed at the tips, such as 116, of all seed holder tubes, such as 79;

the seed catcher 80 is actuated to move the bars 90 and 92 away from the tips such as 116 of seed holder tubes such as 79;

actuator 78 is energized to lower the tube block 83 toward the microtiter plate 58 until the tips such as 116 of the tubes such as 79 are inside the wells such as 59 of row 106, which typically places the tips such as 116 about 4 mm away from the bottom of the wells;

valves, such as 152, are actuated to shift the vacuum "off" and pressure (set at regulator 166) "on" to all the seed holder tubes such as 79 to release the seeds and project them from the tips such as 116 and into each well in row 106, and onto the sticky surface forming the bottom of the wells;

actuator 78 is energized to raise the tube block 83 back to the upper position and valves, such as 152, are actuated to shift the pressure "off" and the vacuum "on" to tubes such as 79;

the transport mechanism 42 moves the overhead module 46 to position the camera 48 over row 106 where the seeds were just placed. The camera "reads" the wells and confirms that a single seed has been properly placed in all wells in row 106, except one, and discovers there is no seed in the target and no seed in the bottom of one well in the row, and the control device 20 notes this in an error data file;

the control device 20 turns "off" the two-way valves 160 to all seed holder tubes except the seed holder tube for the one well that is missing a seed;

the control device 20 commands the transport mechanism 42 to align the overhead module 46 over the seed supply station 34;

the actuator 78 is energized to lower the tube block 83 until the tips such as 116 are in the fluidized bed of seeds in the seed trough 98 (for some seeds, the tip is best located just above the upper surface of the fluidized seeds, for other seeds, the tip is best located just at the surface of the fluidized seeds and for some others the tip is located just below the surface of the fluidized seeds);

the actuator 78 dwells from about 0.01–10 seconds while vacuum is applied to only the one tube to engage a single seed;

the actuator is energized to raise the tube block 83 back to the upper position;

the seed catcher 80 is actuated to move the bars 90 and 92 toward the tips such as 116 of seed holder tubes such as 79 to put the bars in position to catch any seeds falling from the ends of the tubes;

the transport mechanism 42 moves the overhead module 46 over row 106 in plate 58 with the tube block aligned over the row 106;

the seed catcher 80 is actuated to move the bars 90 and 92 away from the tips such as 116 of seed holder tubes such as 79;

actuator 78 is energized to lower the tube block 83 toward the microtiter plate 68 until the tips such as 116 of the tubes such as 79 are inside the wells such as 59 of row 106;

the appropriate valve, such as 152, is actuated to shift the vacuum "off" and pressure "on" to the appropriate seed holder tube 79 to release the seed from the one tube and project it from the tip 116 of that tube and into the well that was previously missing a seed;

actuator 78 is energized to raise the tube block 83 back to the upper position and the appropriate valve, such as 152, is actuated to shift the pressure "off" and the vacuum "on" to the appropriate tube such as 79;

the transport mechanism 42 moves the overhead module 46 to position the camera 48 over row 106 where the missing seed was just placed. The camera "reads" the wells and discovers there are now single seeds in the target for all wells;

the control device 20 turns "on" the two-way valves, such as 160, to all seed holder tubes that had previously been turned "off";

the control device 20 commands the transport mechanism 42 to align the overhead module 46 over the seed supply station 34;

after picking up seeds on all tubes such as 79, the control device will command the transport mechanism to position the overhead module over the next row of wells in the microtiter plate and the process will continue until all wells on all plates in the carrier have at least one seed;

the control device 20 will alert the operator to remove the carriage from the enclosure and notifies the operator about plates that require corrective action;

the operator places any plate requiring corrective action in the seed correcting station 24;

the control device identifies the plate with information from bar code scanner 144 and illuminates the LED or LEDs beneath the wells that require corrective action;

the operator takes corrective action on each well requiring it. Upon completing each plate, the operator actuates the input switch 142 to notify the control device 20 to turn off the LEDs to the corrected wells and update the control device data files to indicate manual correction to this microtiter plate is complete.

While the method and apparatus of the present invention is described in detail above with respect to an herbicide assay, this technology can also be used effectively for other assays such as an insecticide assay.

When handling insect eggs with the system just described for seed handling, there are a few variations in the procedure. It may be desired to place the eggs on the inside surface of an elastomeric lid for a microtiter plate, and it may be desired to use a square well microtiter plate that has wells about 1¾" deep so there is adequate space for the insect larve and insect to develop. The elastomeric lids have square protrusions that extend into each square well of the microtiter plate, and each protrusion has two holes in the corners of the protrusion for entry of oxygen for the larve and insect when the lid is in place over the well. A sticky drop of larve support and growth medium is placed on the inside surface or each lid protrusion to hold the eggs in place and support the eggs until the larve hatches. Only lids are placed in the enclosure 28 on the carrier 38 with the inside surface of the lid facing upward. The seed supply station 34 would be used to supply the eggs in much the same way it is used to supply seeds. The overhead module 46 would be much the same for handling and monitoring eggs as for seeds. After placement of the eggs on the lids, the lids are removed from the enclosure and manually placed on the matching microtiter plate for the lid. After hatching, the larve drops into the well and onto the surface of a mix of larve/insect support medium and test compound in the well that fills the well to a height of several millimeters. The effect of the compound on the larve/insect can be observed over a period of time.

FIG. 10A shows a partial perspective view of an inverted microtiter lid 172 and egg pickup tubes, such as tube 174, for handling insect eggs, such as 176. If there is a problem with the elastomeric lids distorting when laid free and held only by gravity, one can force them to lay flat for the accurate positioning needed for accurate reliable egg placement, using a weighted frame 178 laid on top of the inverted lid held in place on a carrier 179 (similar to the microtiter plate carrier 38). The frame 178 includes a peripheral rim 180 and central rims 182 and 183 to hold the edges, such as lid edge 184, and central part of the lid, respectively, in a flat condition. The lid 172 has a plurality of protrusions, such as protrusion 186, that are arranged to extend into each well of a microtiter plate (not shown). Each protrusion has a hole in two corners of the protrusion, such as holes 188 and 190 in protrusion 186.

FIG. 10B shown an enlarged section side view of a protrusion of a lid and an egg pickup tube. One or more eggs 176 are held on the tip 192 of tube 174 by application of vacuum to the tube. A hole (not shown) extending through tip 192, similar to the hole in seed tube 79 of FIG. 6, is sized to be a slightly smaller diameter than the minor dimension of a single insect egg, which may have a slightly irregular spherical shape. Because of the irregular shape of the eggs, the vacuum flow can extend around each egg so several eggs can be picked up at one time. The number of eggs picked up can be controlled by adjusting the level of vacuum applied through the hole in tip 192. On top of protrusion 186 is a drop 194 of sticky material for holding the eggs and providing some nutrient for the eggs. When depositing the eggs on top of the protrusion 186, the tip 192 of tube 174 is lowered to within a closely spaced distance 196 of about 4 mm from the surface of the drop so the eggs will be reliably deposited onto the sticky drop when the vacuum is shut off and a pressure is applied to the hole in tip 192. After placing eggs on the top of a row of protrusions, the camera monitor 48 would be positioned over this row of protrusions and would monitor each protrusion in the row to determine if there were some eggs placed there. If there were no eggs present, the control system would tell the transport mechanism to go get eggs for the protrusion missing them, similar to the procedure followed for handling seeds.

Variations in the operation of the seed or egg handling and monitoring system is possible without departing from the basic teachings of the invention. For instance, while normally one and only one seed is desired in each well, there could be circumstances where more than one seed and more than one plant would be desired in each well, such as if the weed being evaluated were sedge, which is extremely small and is a common weed problem in rice crops. In such circumstance, it would be most convenient to simply repeat the deposition of single seeds the appropriate number of times. Other variations of the invention include different camera monitoring strategies and the use of automated carrier handling. In addition, the carrier may be replaced with a precision indexing conveyor that will accurately move one plate at a time into a seed depositing position under a simplified transport mechanism. Plates would be automatically loaded onto the conveyor. The simplified transport mechanism would only move in the X-direction 68 and Z-direction 82, and there would only be two possible X positions. One X position would be with the seed pickup tubes over the seed supply station and at the same position, the camera is over the depositing station monitoring the seed placement. The other X-position would be with the seed pickup tubes over the seed depositing station. The indexing conveyor would position the relevant row of wells at the depositing station. The other wells not at the depositing station would be covered under a shield so the seed catcher 80 could be eliminated.

Assay Scoring

Several assays were evaluated for scoring the microscreen. A visual assay was used initially and has continued to be used throughout the development of the microscreen because of its simplicity and similarity to standard greenhouse herbicide assays. This assay worked well for the microscreen and, given only several hours of training and experience, can be learned and reproducibly performed by anyone knowledgeable about plants. Several other scoring assay formats were evaluated.

Visual Assay: Plants were scored visually. Size, morphology, and color were taken into consideration and a score of 0 to 4 was assigned. Table 4 describes the rating system that was adopted for visual assay scoring.

TABLE 4

| System for rating plants for herbicidal injury. | |
|---|---|
| Rating | % Visual Injury |
| 0 | No injury relative to controls |
| 1 | 1–25% injury relative to controls |

TABLE 4-continued

System for rating plants for herbicidal injury.

| Rating | % Visual Injury |
|---|---|
| 2 | 26–50% injury relative to controls |
| 3 | 51–75% injury relative to controls |
| 4 | 76–100% injury relative to controls |

Biomass Assay: Individual plants were removed from the microtiter wells, blotted briefly on paper towels to remove adhering water and then their mass was determined using an analytical balance (Mettler AE50).

Chlorophyll Assay: Other assays were also developed which, compared with the visual and biomass assays, might be more easily automated. An assay which measures chlorophyll content of the plants was developed which requires neither the removal of the plants from the microtiter plate wells nor the grinding of the plant material. This was accomplished by taking advantage of the fact that DMSO will solubilize chlorophyll from intact plant tissue (Hiscos, J. D. and Israelstam, G. F. Can. J. Bot. (1979) 57, 1332–1334). However, the DMSO was not able to extract chlorophyll from plant material when the DMSO was added directly to the plants and agarose in the microtiter plates. The water in the agarose (~100 uL) diluted the 200 uL of DMSO sufficiently that it could not solubilize the chlorophyll. To circumvent this problem, the water in the agarose and plant material was removed by lyophilization. DMSO then readily extracted the chlorophyll from the resulting dried agarose and plant material. Because of the simplicity of this assay, it is not only easily performed manually but also can be readily automated.

Several tests were conducted to validate the chlorophyll assay. In order to determine whether the chlorophyll assay was a good measure of overall plant growth, a set of 95 Arabidopsis plants which were variable in size (biomass coefficient of variation=0.63) were removed from the microtiter plate and their fresh biomass was determined using an analytical balance. The plants were then returned to the microtiter plate wells and their chlorophyll content was measured.

Microtiter plates were frozen at −20° C. and then lyophilized. DMSO (200 uL) was added to each well and the plates were incubated in the dark at 65° C. for 1 h with gentle shaking (about 30 rpm). Plates were then cooled to room temperature in the dark. The absorbance of the DMSO solution was then measured in a Molecular Devices VMAX™ Kinetic Microplate reader. The absorbance at 650 nm (near the peak of the chlorophyll absorbance spectra) was corrected for scattering by subtracting from it the absorbance at 562 or 570 nm, wavelengths were chlorophyll has essentially no absorbance. This difference is termed $\Delta(A650-A562)$ and $\Delta(A-650-A570)$, respectively, and is used as a measure of the chlorophyll content of the plant in a given well. It would be possible to empirically determine the extinction coefficient for $\Delta(A650-A562)$ and $\Delta(A650-A570)$ for chlorophyll in DMSO in order to convert these values to absolute quantities of chlorophyll. However, the nature of the microscreen assay requires only relative (i.e., not absolute) measures of plant growth.

Figure 2:
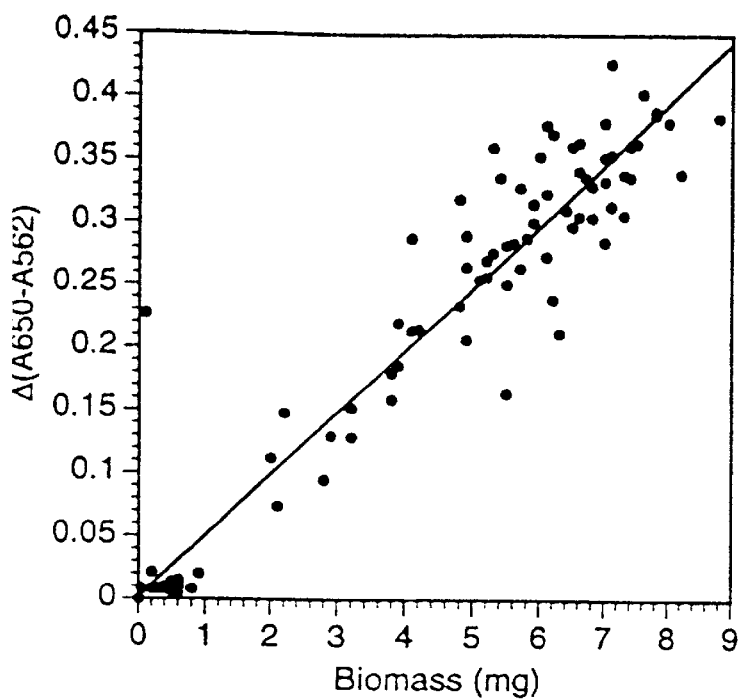
FIG. 2. Correlation of biomass and chlorophyll assays. Ninety-five Arabidopsis plants from a single, 14-day old microscreen plate were assayed both for biomass and chlorophyll. Each data point represents a single plant. The line was calculated by least square regression using a linear model and has a correlation coefficient, $r^2=0.91$. As can be seen, there is a high correlation between plant biomass and chlorophyll content, validating the chlorophyll assay as a positive indicator of plant growth.

FIG. 2 shows a comparison of the biomass and chlorophyll content of each plant. The excellent fit of the results to a straight line (correlation coefficient, $r^2=0.91$) indicates that chlorophyll content is directly proportional to biomass. Inspection of the data indicates that all but one of the plants closely fits this proportionality. Visual scoring indicates that the single exception was probably due to an error in measuring the biomass rather than the chlorophyll.

Figure 3A:
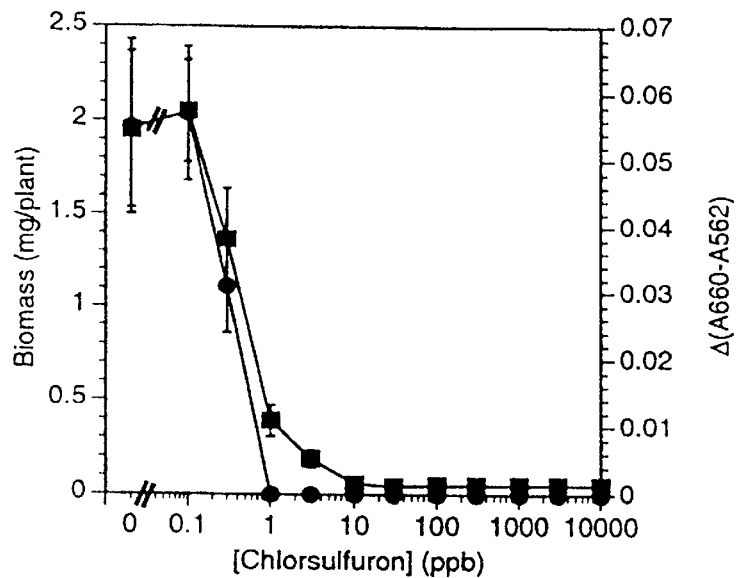
FIGS. 3A and B. Effects of chlorsulfuron and norflurazon on Arabidopsis as measured by chlorophyll and biomass assays. Plants were grown in the microscreen on the indicated level of chlorsulfuron or norfluorazon for 14 days. The biomass of individual plants was then determined. Plants were then placed back into the wells and their chlorophyll content was measured. Each point represents the mean of 8 replicates and error bars represent the standard error of the mean. As can be seen, the dose response curve that results from the biomass assay is very similar to the dose response curve resulting from the chlorophyll assay, indicating that the chlorophyll assay is an accurate measure of herbicidal activity.
Figure 3B:
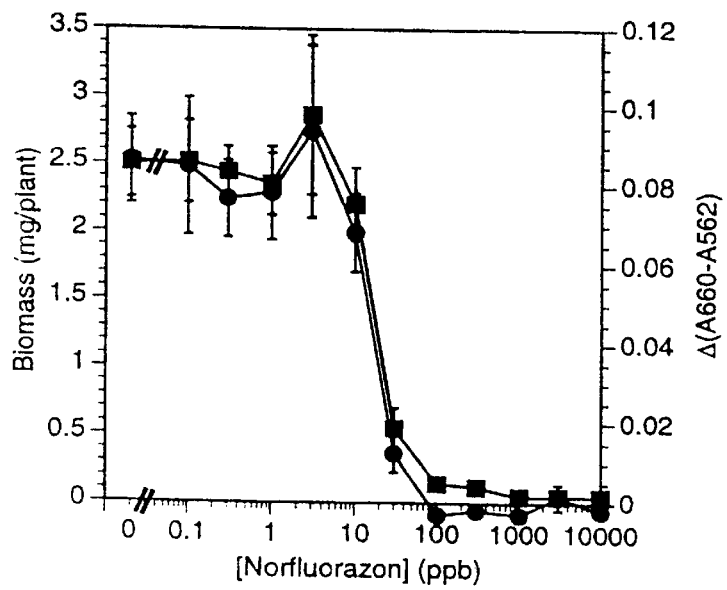

In order to determine whether the chlorophyll assay would provide a good measure of herbicidal damage, the responses to two herbicides which produce different types of injury were measured both by biomass and by the chlorophyll assay. Damage caused by the herbicide chlorsulfuron is manifested in the microscreen by reduced plant growth. In contrast, the herbicide norfluorazon produces plants which germinate and have expanded cotyledons, but which lack chlorophyll. FIGS. 3A and B show the responses of Arabidopsis plants grown in the microscreen and treated with a range of concentrations of chlorsulfuron and norfluorazon. In each case, the dose response curve as measured by the biomass assay is very similar to that measured by the chlorophyll assay.

Other Assays: Other assays for herbicidal damage can also be used, including computerized analysis of images of the plants. This assay should allow the rapid, automated, and non-destructive determination of the size, level of pigmentation and morphology of the plants without removing them from the microtiter plates.

A second assay which can be used relies on the kinetics of chlorophyll fluorescence as a measure of plant health. Like the image analysis assay, this assay will also be rapid, automated, and non-destructive. Unlike most of the other assays, this assay will provide a measure of the health of the plant at the time the assay is conducted, rather than a cumulative measure of the plant health during the course of the growth period. For this reason, it may provide a useful alternative means of quantifying rapid herbicidal damage.

A third assay utilizes reporter genes (e.g. luciferase, beta-glucuronidase, green fluorescent protein, anthocyanin biosynthetic enzymes, etc.) under the control of constitutive, tissue-specific or environmentally inducible regulatory elements. For this type of assay, plants used for the microscreen would be transformed with constructs containing these reporter genes and the appropriate regulatory elements. For example, luciferase activity can be rapidly and sensitively quantified from intact plants grown in microtiter plates in a non-destructive manner using a luminometer. If the luciferase gene is controlled by a constitutive regulatory element, then the total luciferase activity will be dependent on the total biomass of the plant. If a root-specific regulatory element were used to control the luciferase, then the luciferase activity would measure the amount of root biomass present on the plant. If a stress-induced regulatory element is used to control the luciferase, then the stress produced by a particular compound could be measured directly. Stress-induced regulation of luciferase offers the possibility of detecting chemically-induced stress at test compound concentrations which are below that required to produce visible damage to the plant, thus decreasing the amount of compound required for screening.

A fourth assay utilizes expression of the calcium-sensitive luminescent protein apo-aequorin to monitor the level of calcium present in specific compartments and tissues of plants. Variation of calcium levels caused by application of test compounds can be monitored by detection and measurement of luminescence mediated by the reconstituted aequorin. This variation is indicative of changes in cellular metabolism and would therefore serve as a sensitive measure of stress induced by application of herbicidally active compounds.

Species Sensitivity to Herbicide Lead Compounds and Greenhouse-Inactive Compounds The sensitivity of plant species in the microtiter plate assay was evaluated by testing 11 previously selected plant species against a library of 105 compounds known to have herbicidal activity as demonstrated in traditional greenhouse primary screens. Compounds which demonstrated no herbicidal activity in the greenhouse were also included in the evaluation.

Plates were prepared as previously described. A single seed of a plant species was seeded into a microwell containing 100 uL of ½× MS media in agarose containing 10 ppm of test compound or DMSO for a control. Each treatment was replicated 8 times per species (one column) in each test plate.

A total of 105 herbicidally active compounds and 50 compounds which were inactive in traditional greenhouse primary screens were tested in the whole plant microtiter plate assay. Results for greenhouse active chemistry are presented in Table 5, and results for greenhouse inactive compounds are presented in Table 6.

TABLE 5

Sensitivity of Plant Species to Lead Herbicidal Compounds.

| Plant Species | Very Active (3–4 rating) | Active (1–2 rating) | Inactive (0 rating) | % Active |
|---|---|---|---|---|
| Arabidopsis thaliana | 61 | 37 | 7 | 93 |
| Asrostis stolonifera | 40 | 15 | 50 | 52 |
| Browallia speciosa | 43 | 20 | 42 | 60 |
| Coleus blumei | 29 | 21 | 55 | 48 |
| Digitalis purpurea | 45 | 26 | 34 | 68 |
| Digitaria sanguinalis | 33 | 26 | 46 | 56 |
| Inula Ensifolia | 30 | 37 | 38 | 64 |
| Nicotiana tabacum | 50 | 25 | 30 | 71 |
| Oxalis stricta | 36 | 29 | 40 | 62 |
| Panicum coloratum* | — | — | — | — |
| Petunia hybrida | 58 | 26 | 21 | 80 |

*Panicum coloratum was not evaluated due to poor germination.

TABLE 6

Sensitivity of Plant Species to Compounds Herbicidally Inactive in the Greenhouse.

| Plant Species | Very Active (3–4 rating) | Active (1–2 rating) | Inactive (0 rating) | % Active |
|---|---|---|---|---|
| Arabidopsis thaliana | 4 | 12 | 34 | 32 |
| Asrostis stolonifera | 0 | 1 | 49 | 2 |
| Browallia speciosa | 2 | 3 | 45 | 10 |
| Coleus blumei | 0 | 4 | 46 | 8 |
| Digitalis purpurea | 2 | 6 | 42 | 16 |
| Digitaria sanguinalis | 0 | 1 | 49 | 2 |
| Inula Ensifolia | 0 | 3 | 47 | 6 |
| Nicotiana tabacum | 2 | 6 | 42 | 16 |
| Oxalis stricta | 0 | 10 | 40 | 20 |
| Panicum coloratum* | — | — | — | — |
| Petunia hybrida | 6 | 7 | 37 | 26 |

*Panicum coloratum was not evaluated due to poor germination.

These data indicate that plants used in the herbicide microscreen were very sensitive biological indicators, with 99% of the lead compounds and 32% of the inactive compounds expressing visually detectable injury to at least one plant species. Arabidopsis and Petunia are the most sensitive species tested with 93 and 80% of the lead molecules showing herbicidal effects, respectively. Coleus, Asrostis, and Digitaria were generally less sensitive with 48, 52, and 56% of the lead compounds showing activity, respectively. Of the lead compounds tested, 80% were "very active" (visual rating score of 3 or 4) against at least one species, as compared with 16% of the greenhouse inactive compounds.

Whole Plant High-Throughput Screen Evaluation

Seven plant species (Arabidopsis, Browallia, Coleus, Digitaria, Nicotiana, Oxalis and Petunia) were selected for final evaluation of the whole plant microscreen based on uniformity of growth, germination, and biological sensitivity to herbicidal compounds determined from previous experiments.

Chemical compounds (both active and inactive) were randomly selected from both internal and external sources which had been previously tested in the traditional greenhouse primary herbicide screen. Plates were prepared as shown above. A total of 14 treatment plates were prepared from each daughter plate for evaluation of seven plant species and two replications of each species.

Data from the 2024 compounds tested in the microscreen are summarized and compared with general greenhouse activity in Table 7.

TABLE 7

Comparison between microscreen and greenhouse herbicidal activity.

| Plate | Micro Scr Advanced[1] | Greenhse Active[2] | Greenhse Advanced[3] | Non Micro Grnhse hits[4] | Non Micro Grnhse Advanced[5] |
|---|---|---|---|---|---|
| 1 | 10 | 5 | 4 | 1(2) | 0 |
| 2 | 12 | 1 | 0 | 0 | 0 |
| 3 | 5 | 2 | 1 | 0 | 0 |
| 4 | 5 | 6 | 2 | 3(2,2,2) | 0 |
| 5 | 9 | 2 | 0 | 0 | 0 |
| 6 | 7 | 4 | 2 | 0 | 0 |
| 7 | 17 | 1 | 0 | 0 | 0 |
| 8 | 8 | 1 | 1 | 1(4) | 1 (broadly active) |
| 9 | 4 | 2 | 1 | 1(3) | 0 |
| 10 | 9 | 5 | 2 | 2(1,2) | 0 |
| 11 | 8 | 5 | 2 | 1(2) | 0 |
| 12 | 10 | 1 | 0 | 1(1) | 0 |
| 13 | 10 | 1 | 1 | 0 | 0 |
| 14 | 10 | 1 | 0 | 0 | 0 |
| 15 | 14 | 4 | 0 | 2(2,2) | 0 |
| 16 | 13 | 1 | 0 | 1(1) | 0 |
| 17 | 10 | 3 | 0 | 0 | 0 |
| 18 | 12 | 6 | 3 | 1(2) | 0 |
| 19 | 11 | 6 | 0 | 1(2) | 0 |
| 20 | 9 | 0 | 0 | 0 | 0 |
| 21 | 8 | 5 | 0 | 3(1,1,2) | 0 |
| 22 | 13 | 1 | 0 | 0 | 0 |
| 23 | 11 | 0 | 0 | 0 | 0 |
| Totals | 225 | 63 | 19 | 18 | 1 |
| % Advanced | 11.1 | 3.1 | 1.0 | | |

[1]Compounds showing significant activity, i.e., replicated activity on a single species of greater than 2, or moderate activity, i.e., replicated activity on more than one species of less than or equal to 2.
[2]Injury level of 50% or greater on one or more species in greenhouse testing.
[3]Compounds advanced for further evaluation from greenhouse testing which have acceptable activity levels in novel chemical areas or known chemical areas of interest.
[4]The number of greenhouse active compounds (column 3) not advanced in the microscreen (column 2). For those compounds not advanced in the microscreen, the number in parentheses indicates a summary of their greenhouse activity using the 0–4 microscreen rating scale.

TABLE 7-continued

Comparison between microscreen and greenhouse herbicidal activity.

| Plate | Micro Scr Advanced[1] | Greenhse Active[2] | Greenhse Advanced[3] | Non Micro Grnhse hits[4] | Non Micro Grnhse Advanced[5] |
|---|---|---|---|---|---|

[5]The number of greenhouse advanced compounds (column 4) not advanced in the microscreen (column 2). For those compounds not advanced in the microscreen, a description of greenhouse activity is provided in parentheses.

Very High Density Array Plates and Applications

Another preferred embodiment of this invention employs very high density arrays of seeds or plants grown from seeds in a plate such as that described below.

Microplate Designs

A microplate has been developed for use in high throughput or low volume in vitro assays. This microplate is suitable for the growth of plants and screening of biological activity according to the present invention. The microplate is preferably rectangular, being approximately 125 mm long, 85 mm wide and 4 mm thick. Use of these dimensions allows the plate to be handled and indexed by currently available devices for automated microtiter plate handling. However, unlike conventional microtiter plates, the microplate of the present embodiment may contain a very large number of very small microwells. Preferably each of the microwells has a depth of approximately 1 mm and a volume of approximately 0.5 μl or less. The preferred microplate of this invention has 9600 microwells, each having a volume of approximately 0.2 μl, arranged in 120 rows and 80 columns. Each of the microwells has an inlet that forms an approximately 1 mm square. However a lesser number of microwells, for example 2400 microwells, each having a depth of approximately 3 mm and a volume of approximately 5 μl, arranged in 60 rows and 40 columns, may also be preferred. In this embodiment, each microwell has an inlet that forms an approximately 2 mm square. It should be understood that the microplate according to the current invention could be fashioned in other shapes as well, for example a circular plate having a 125 mm diameter containing 14,500 wells arranged in a honeycomb pattern could be constructed; such a circular arrangement will maximize the use of a circular imaging field.

The small volume microplate described above has a border that surrounds the working portions of the plate. The working portion of the plate consists of microwells formed on the upper surface of the plate. In this embodiment of the invention, the body of each microwell is formed by four walls, each of which extends downward from the inlet. The four walls consist of a first pair of opposing walls and a second pair of opposing walls. Said walls are inclined at an angle to the vertical direction—that is, an angle with respect to a line perpendicular to the plane of the plate. Thus, the microwells have the shape of an inverted four sided pyramid. Preferably, the walls of the microwells are steep, so that the angle from vertical is no greater than approximately 45°, and most preferably, approximately 30° or less. As a result of the steepness of the inclined walls, essentially all of the light incident from the vertical upon the microwells that is not absorbed by the plate material is either reflected away from vertical or reflected to the opposite side of the well, thus preventing "lens effects" which interfere with optical methods (e.g., fluorescence, luminescence, spectrophotometric, etc.) for monitoring the microplates. The bottoms of the microwells are preferably flat, however, other bottom shapes such as arcuate or conical, could also be utilized.

An important aspect of the design of the microplate is that the walls of adjacent microwells intersect along edges so that the boundary between adjacent microwells is a ridge; this avoids the formation of flat, horizontal surfaces that would allow liquid to collect between microwells. Although the present embodiment of the microplate possesses microwells with the shape of a four sided pyramid, other shapes could also be utilized provided that the boundary of between the inlets of adjacent microwells is formed by an edge without any intervening flat, horizontal surfaces that would allow liquid to collect between microwells. Furthermore, the walls of the microwells need not be straight in order to satisfy the requirement that they form sufficiently sharp edges between adjacent microwells. This aspect of the design also facilitates loading of the wells with seeds or other solid or suspended materials, as described below.

The preferred composition of the microplate is a polymeric material, such as liquid crystal polymer, which has essentially no fluorescence with respect to wavelengths in the 300 nm to 650 nm range, which is the range of interest for most biological screening applications. More preferably, the liquid crystal polymer is made into an opaque black material through the addition of one or more pigments, thereby minimizing reflection. However it is understood by the person skilled in the art that other polymeric compositions (e.g., polystyrene) may impart useful properties to the microplate, depending on the intended methods of seed or compound loading and the method of monitoring the results of the assay.

Use of Microplates in Plant Microscreens

Many plant seeds have at least one dimension of size that is smaller than the microwell cross-section described above and thus can be distributed on these density plates such that at least one will occupy a discrete well in the plate. In the case of Arabidopsis, the seeds are significantly smaller than 1 mm in all dimensions so that at least one seed can easily be accomodated in each well. This feature was exploited to generate dense lawns of the plant for high throughput screening of herbicidal compounds. However, it is not a requirement for use in the method of the present invention that a seed fit entirely within the volume of the microwell.

To prepare the microplates for accepting plant seeds, they were rendered sterile by autoclaving or soaking in ethanol. They were then wetted to ensure that air bubbles would not prevent the seeds from settling to the bottom of the wells. Seeding of Arabidopsis was most easily accomplished by suspending a volume of the seeds in approximately three volumes of water and then applying the suspension on the surface of the 9600 well plate, for example, with the aid of a plastic spatula. Where multiple seeds were found to occupy a single well, the excess were readily removed with a damp paint-brush and relocated to any empty wells. A plate was generally seeded with single seeds per well in about 1 hour.

The seeded plates were stored in air-tight containers with lids that could be missed with water and a lower section that could be filled with water or damp towel, to ensure an environment of constant high humidity. The plates were inspected every 24 hours to ensure the seeds were not limited for water or nutrient solution and that germination was proceeding normally and at high frequency. After 5 days at 23° C. the plant had completely emerged from the seed coat and the cotyledons or primary leaves had fully expanded. Plants could be maintained in this way for more than 4 weeks.

The plants can be exposed to compounds to be evalated at two stages of development in these dense formats. The first was a treatment that exposed the pre-emergent seed to compound by applications of known herbicides to the wells that contained the seeds, either during initial imbibing or once the seed-coat had split. The effects of this treatment was compared to seeds that had been treated only with water or a nutrient solution.

Alternatively, compounds to be tested can be added to the plate once the plane had emerged from the seed and the primary leaves had expanded. In this post-emergent application, compounds can be applied to the leaves and the results compared to plants on a section of the plate that had only been treated with water.

These high density plates can accommodate up to 9600 discrete compounds; more, if compounds were applied as mixtures. However, it is clear that there are advantages to applying less than this optimum number so that a statistical analysis of compound effect might be derived by application of one compound to more than one plant. For example if four plants or seeds arrayed in the plate are treated with one compound, then up to 2400 compounds might be accomodated. Ideally areas of treatment might need to be discriminated from one another by separating each treatment with a border of untreated plants or seeds and in this format more than 1000 discrete compounds might be assessed. The treatment of multiple plants in a sector with a given compound, thereby constituting a population of treated plants, no longer requires that every well contain a single seed; it is possible to acquire activity data from a sector of the plate rather than an individual well. In practice, this is a desireable practical feature, as the method of seeding the plates described above does not always result in a uniform distribution of only one seed per microwell.

Compound application on such dense lawns is feasible with the technology that now exists to apply solutions or compound in these densities. Automated solution dispensing devices or methods that can deliver either sub microliter discrete drops spaced less than 1 mm apart or narrow streams of solution, are commercially available, for example the Cartesian A/D3200 aspiration and dispensing device from Biodot Ltd (Cambridge, UK). In a discrete format such equipment could deliver discrete compounds to individual wells or plants. These can also be used with a spray application to expose multiple seeds or plants to a discrete compound in solution. These sprayers might also be used to predeliver a set of compounds to a matrix such that the compounds are applied simultaneously to a seeded plate or a lawn of emerged plants. For example, compounds applied to a mesh or other physical support with cell dimensions approximating those of the well dimensions in the plate acts as a support matrix that carries compound either dry or in solution. The mesh is preferably composed of an inert material such as nylon or polypropylene (e.g., Flowmesh™, Diversified Biotech, Boston, Mass.). The mesh can be laid over pre-emergent seeds or developing plants such that the compound is transferred to the emerging individual. It could be envisaged that a library of compounds be stored on a matrix and to be used when required for pre-emergent or post-emergent applications.

Many chemical compounds are now synthesised combinatorially and immobilised on beads that have dimensions less than the well size of these dense array plates. Application of the beads at the time of seeding and then timed release of the compound from the bead, for example by photolytic cleavage of a light sensitive bond holding the compound to the bead, would provide a means of exposing pre- or post-emerging plants to compounds.

High density arrays of whole plants other than Arabidopsis are feasible. Tobacco and petunia are examples of plants, the seeds of which have some dimension small enough that single seeds occupy each well in the high density plate. Therefore the concept is not limited to just Arabidopsis plants. Furthermore the density of wells per plate is not limiting. As was described above, plates with larger wells that would accommodate up to 2400 individual seeds are included in the concept of this invention. This introduces flexibility into the number and type of plant species or genus that could be introduced into the screens using this format.

Additional applications of the microplate format include the culture of plant material and the addition of a plant pathogen(s) or plant pest(s) (such as insects) which may be evualated in term of their control by compounds applied to the microplate in either pre-emergent or post-emergent and pre-infection or post-infection applications. For example, the powdery mildew pathogen of Arabidopsis, *Erysiphe cichoracearum,* is inoculated onto plants grown in the microplate either following the treatment of the plants with compounds (to assess preventive or prophylactic activities of test compounds) or it is inoculated and allowed to establish a disease complex with the host and compounds are then applied to the plants or released into the wells. This method is applicable to any compatible plant-pathogen combination, the pathogen being a virus, a bacterium or a fungus. The method is also applicable with any compatible plant-pest combination which satisfies the operational criteria of the microplate assay.

Herbicide Waste Stream Reductions

Implementation of the herbicide microscreen has many benefits, including reduced resource and compound requirements, higher throughput capabilities, and a tremendous reduction in the waste stream associated with primary herbicide screening. The material waste stream from the primary herbicide screen can effectively be reduced by >98% using the microtiter plate screening system of the present invention. Additional environmental benefits include significant reductions in acetone emissions from spray applications and less landfill waste since microtiter plates would likely be incinerated.

What is claimed is:

1. A method of automatically depositing a seed into each of a plurality of containers, each container having a cross-sectional area of not greater than 0.5 $cm^2$ and each seed being one that will germinate into a plant of the genus selected form the group consisting of Ageratum, Arabidopsis, Arabis, Artemisia, Asrostis, Browallia, Capsella, Coleus, Cortaderia, Cynodon, Cyperus, Digitalis, Digitaria, Eragrostis, Inula, Ipomopsis, Laevis, Lemna, Nicotiana, Oxalis, Panicum, Petunia, Platycodon, Recta, Sagina, Santolina, Thymophylla, and Thymus, the method comprising providing the seeds in at least one fluidized bed, providing a plurality of vertical hollow seed transport tubes each of such tubes having at its lower end an opening the largest dimension of which is smaller than the smallest dimensions of the seed, each of said tubes having means for controlling the air pressure within the hollow portion of the tube, the air pressure within each tube being individually controllable, positioning the plurality of tubes relative to the at least one fluidized seed beds such that the lower ends of the plurality of tubes is partially immersed in the at least one fluidized seed bed, controlling the air pressure within each tube to create a vacuum within each tube sufficient to capture and hold a seed at the opening at the lower end of each tube, positioning the plurality of tubes relative to the containers such that the lower end of each tube is within a container, positioned approximately in the center of the horizontal cross section of each container, below the level of the top of the container and above the level of any contents in the container, controlling the air pressure within each tube to release the vacuum and create pressure within each tube higher than the pressure outside each tube sufficient to release and expel the seed into the container, and automatically detecting whether one and only one seed has been placed in a predetermined target area in each of the plurality of containers, and recording which containers have not had one seed so placed.

2. The method of claim 1 further comprising having in each container before the seed is expelled therein a substance which when contacted by the seed will inhibit or prevent further movement of the seed within the container and inhibit or prevent the seed from being expelled from the container due to air currents resulting from any excess air pressure within the tube.

3. The method of claim 1 further comprising detecting whether each container has had placed therein one and only one seed, and correcting the seeding of any container found not to contain one and only one seed.

4. An apparatus for automatically depositing a plant seed or insect egg into each of a plurality of containers comprising a plurality of vertical hollow seed or egg transport tubes, each of such tubes having at its lower end an opening the largest dimension of which is smaller than the smallest dimension of the seed or egg, each of said tubes having means for individually controlling the air pressure within the hollow portion of the tube, and a means for automatically detecting whether one and only one seed or egg has been placed in a predetermined target area in each of the plurality of containers, and for recording which containers have not had one seed or egg so placed.

* * * * *